United States Patent
Ogata et al.

(10) Patent No.: US 10,433,798 B2
(45) Date of Patent: Oct. 8, 2019

(54) APERTURE, COLLIMATOR, AND X-RAY TOMOGRAPHIC IMAGING APPARATUS

(71) Applicant: General Electric Company, Schenectady, NY (US)

(72) Inventors: Kentaro Ogata, Tokyo (JP); Kotaro Yamaura, Tokyo (JP); Brandon Allan Smith, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 214 days.

(21) Appl. No.: 15/719,955

(22) Filed: Sep. 29, 2017

(65) Prior Publication Data

US 2019/0099136 A1 Apr. 4, 2019

(51) Int. Cl.
*A61B 6/00* (2006.01)
*A61B 6/03* (2006.01)
*A61B 6/06* (2006.01)

(52) U.S. Cl.
CPC .............. *A61B 6/405* (2013.01); *A61B 6/032* (2013.01); *A61B 6/06* (2013.01)

(58) Field of Classification Search
CPC .......... A61B 6/032; A61B 6/06; G01T 1/2985
USPC ........................................................ 378/147
See application file for complete search history.

(56) References Cited

U.S. PATENT DOCUMENTS

| | | | | |
|---|---|---|---|---|
| 7,170,975 B2* | 1/2007 | Distler | ................... | A61B 6/032 378/147 |
| 2006/0078083 A1* | 4/2006 | Nishide | ................... | A61B 6/032 378/16 |
| 2010/0119033 A1* | 5/2010 | Li | ............................ | A61B 6/06 378/5 |
| 2014/0050296 A1* | 2/2014 | Ying | ....................... | A61B 6/032 378/7 |
| 2015/0245804 A1* | 9/2015 | Kieft | ....................... | A61B 6/06 378/147 |
| 2019/0029614 A1* | 1/2019 | Choi | ....................... | A61B 6/00 |

FOREIGN PATENT DOCUMENTS

JP 2009-050361 A 3/2009

* cited by examiner

*Primary Examiner* — Yara B Green

(57) ABSTRACT

An aperture comprises blocking members and for blocking X-rays. The blocking member has: an edge formed on an arc A1 lying on a circumference CF2 of a circle with radius r2 around a focal spot f in an XY-plane; an edge connected to one endpoint of the edge, the edge being formed to lie on the side of the X-ray detector with respect to an arc A11 contiguous to the arc A1; and an edge connected to the other endpoint of the edge, the edge being formed to lie on the side of the X-ray detector with respect to an arc A12 contiguous to the arc A1. The blocking member has: an edge formed on an arc A2 lying on the circumference CF2 of the circle with radius r2 around the focal spot f in the XY-plane; an edge connected to one endpoint of the edge, the edge being formed to lie on the side of the X-ray detector with respect to an arc A21 contiguous to the arc A2; and an edge connected to the other endpoint 23*b* of the edge, the edge being formed to lie on the side of the X-ray detector with respect to an arc A22 contiguous to the arc A2.

12 Claims, 36 Drawing Sheets

FIG. 5
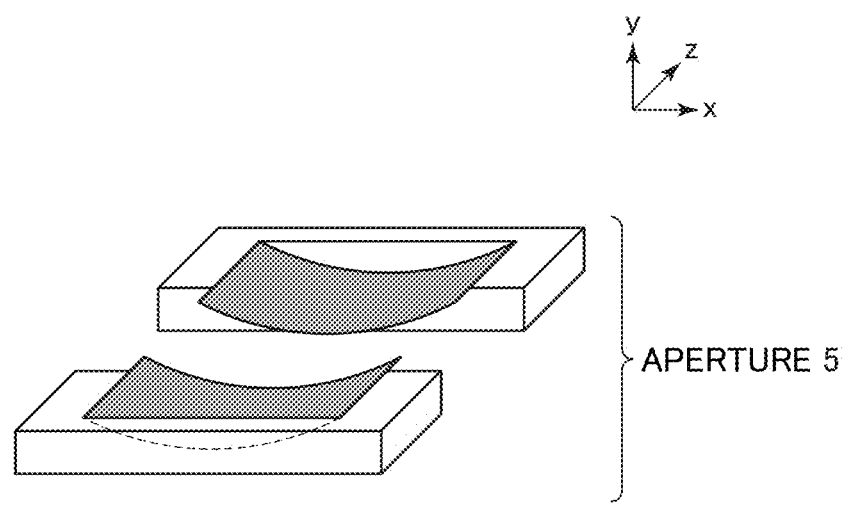
APERTURE 5
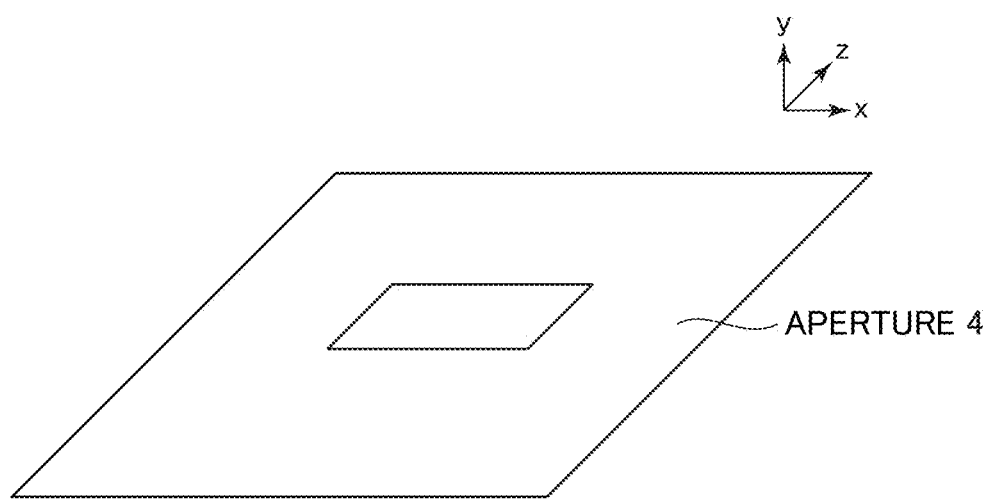
APERTURE 4

FIG. 28
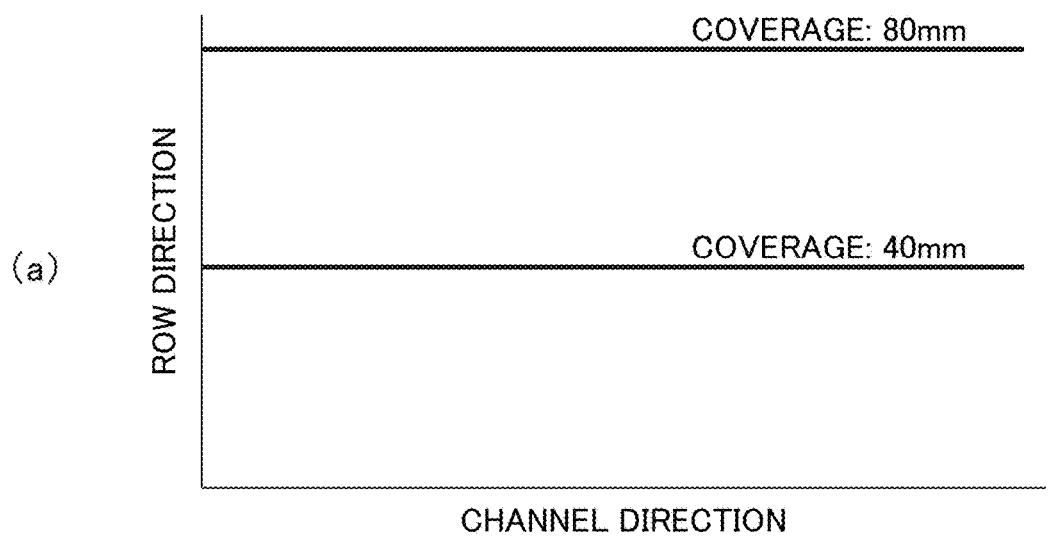
(a)
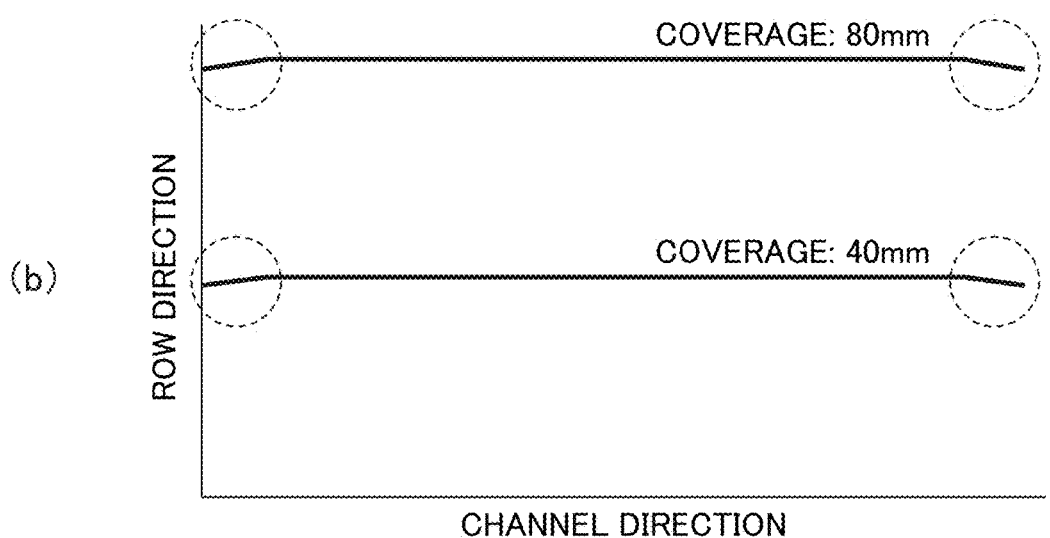
(b)

APERTURE, COLLIMATOR, AND X-RAY TOMOGRAPHIC IMAGING APPARATUS

FIELD OF THE INVENTION

The present invention relates to an aperture having a blocking member for blocking X-rays, a collimator having such an aperture, and an X-ray tomographic imaging apparatus having such an aperture.

BACKGROUND OF THE INVENTION

An X-ray tomographic imaging apparatus has an aperture for defining a range of X-ray impingement to prevent as many X-rays as possible from impinging upon the outside of a body part of interest (PTL 1: Japanese Patent Application KOKAI No. 2009-050361).

BRIEF DESCRIPTION OF THE INVENTION

In PTL 1 is disclosed a CT tomography apparatus comprising an arcuate detector and a collimator having collimator plates for blocking X-rays. PTL 1 discloses that the spacing (aperture width) between the collimator plates in the collimator is adjustable. Thus, the range in which X-rays impinge may be adjusted according to the size of a body part to be imaged. However, because the collimator according to PTL 1 uses flat plates for the arc-shaped detector, the shape of a region onto which an X-ray beam is projected significantly varies depending upon the plate-to-plate spacing (aperture width), posing a problem that it is difficult to keep an X-ray beam in an ideal shape.

Accordingly, a method of shaping an X-ray beam using a collimator having arc-shaped blades has been developed taking account of the arc shape of the detector.

By using the arc-shaped blades, it is possible to form an ideal rectangular shape of the projected region.

In X-ray imaging, it is important to reduce a subject's radiation exposure during a scan to be examined as much as possible. Accordingly, there is known a beam tracking technique comprising, to reduce a subject's radiation exposure during a scan, forming penumbra regions onto four corners of a detector, and controlling the position of collimator plates based on a change of X-ray intensity detected in the four corners of the detector.

Since the beam tracking technique is effective in reducing a subject's radiation exposure during a scan, a variety of beam tracking techniques have been developed. However, the arc-shaped blades pose a problem that penumbra regions cannot be formed on a detector when the aperture width is maximized, and beam tracking cannot be applied.

Therefore, it is desired to develop a collimator comprising an aperture suitable for beam tracking.

The present invention, in its first aspect, is an aperture used in an X-ray togomoraphic imaging apparatus comprising an X-ray tube and a X-ray detector. The X-ray detector has a plurality of detector elements arranged in first and second directions. The first direction is along a circumference of a first circle with radius r1 around a focal spot of the X-ray tube in a first plane perpendicular to the body-axis direction, and the second direction is parallel to the body-axis direction. The aperture comprises a first blocking member for blocking X-rays and a second blocking member for blocking X-rays. The second blocking member is disposed in the second direction with respect to the first member. Each of the first and second blocking members has a first edge, a second edge, and a third edge. The first edge is formed on a first arc lying on a circumference of a second circle with radius r2(<r1) around the focal spot of the X-ray tube in the first plane. The second edge is connected to one endpoint of the first edge, and is formed to lie on a side of the X-ray detector with respect to a second arc lying on the circumference of the second circle and contiguous with the first arc. The third edge is connected to another endpoint of the first edge, and is formed to lie on the side of the X-ray detector with respect to a third arc lying on the circumference of the second circle and contiguous with the first circle on a side opposite to the second arc.

Since a penumbra may be created on an X-ray detector by the first and second edges, an aperture suitable for beam tracking may be obtained.

The present invention, in its second aspect, is a collimator comprising the aperture as described regarding the first aspect.

The present invention, in its third aspect, is a radiation an X-ray tomographic imaging apparatus comprising the aperture as described regarding the first aspect.

BRIEF DESCRIPTION OF THE DRAWINGS

FIG. 5 is a perspective view of apertures, which are a main portion of the collimator 731;

FIG. 28 is a diagram showing graphs representing beam coverage;

DETAILED DESCRIPTION OF THE INVENTION

Now embodiments for practicing the invention will be described, although the present invention is not limited thereto.

(1) First Embodiment

Figure 1:
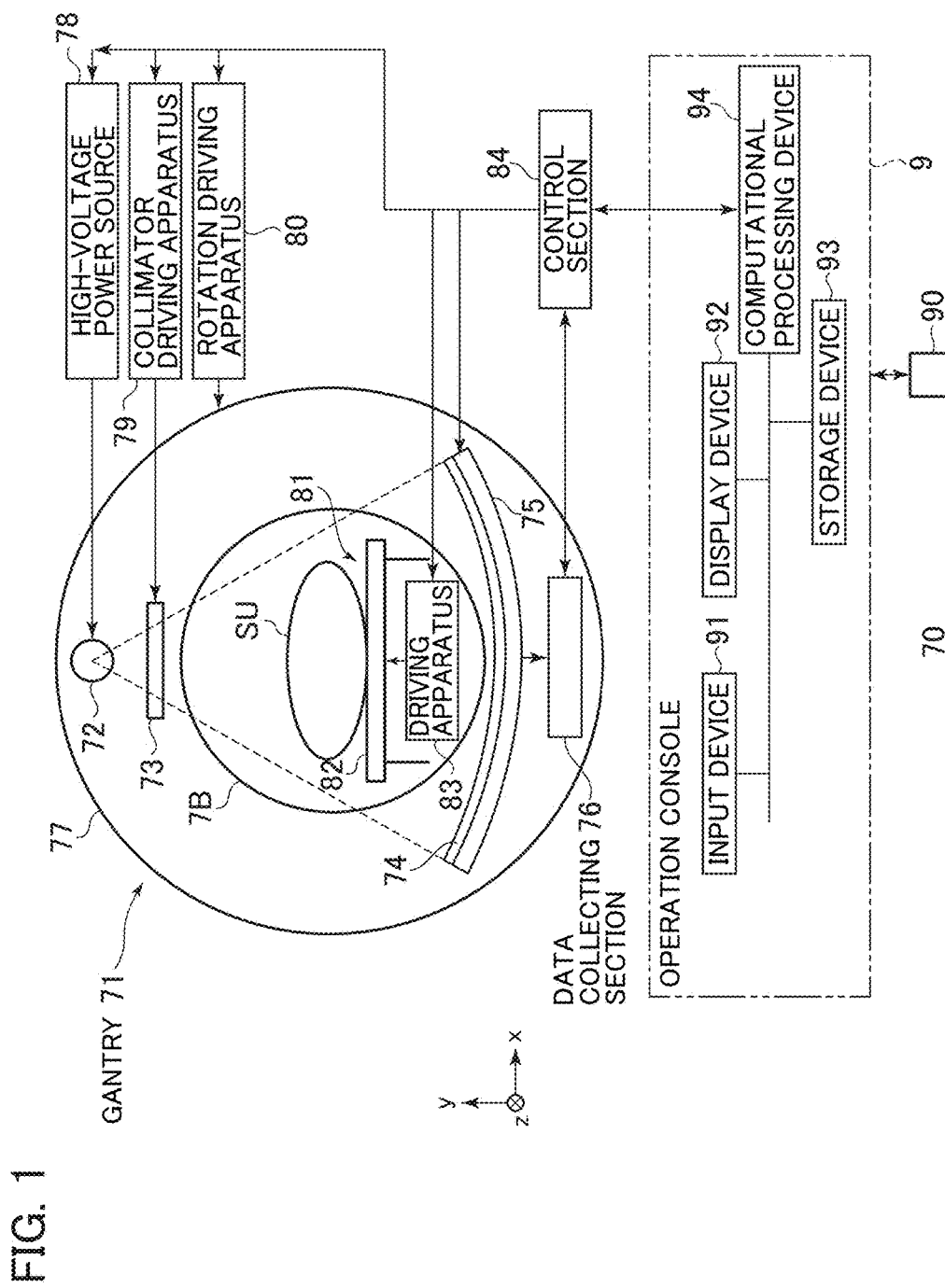
FIG. 1 is a diagram schematically showing a hardware configuration of an X-ray CT apparatus 70 in accordance with a first embodiment.

FIG. 1 is a diagram schematically showing a hardware configuration of an X-ray CT apparatus 70 in accordance with a first embodiment.

As shown in FIG. 1, a gantry 71 comprises an X-ray tube 72, a first collimator 73, a second collimator 74, an X-ray detector 75, a data collecting section (data acquisition system) 76, a rotating section 77, a high-voltage power source 78, a collimator driving apparatus 79, a rotation driving apparatus 80, and a control section 84.

The rotating section 77 is rotatably supported. The X-ray tube 72, first collimator 73, second collimator 74, X-ray detector 75, and data collecting section 76 are mounted on the rotating section 77.

The X-ray tube 72 and X-ray detector 75 are disposed to face each other sandwiching an imaging volume, i.e., a bore 7B of the gantry 71, in which a subject to be examined SU is placed.

The first collimator 73 is disposed between the X-ray tube 72 and bore 7B. The first collimator 73 shapes X-rays emitted from an X-ray focal spot of the X-ray tube 72 toward the X-ray detector 75 into a fan or cone beam.

The second collimator 74 is disposed between the bore 7B and X-ray detector 75. The second collimator 74 removes scatter rays that would otherwise impinge upon the X-ray detector 75.

The X-ray detector 75 comprises a plurality of X-ray detector elements. Each X-ray detector element detects X-rays passing through the subject SU laid in the bore 7B, and outputs an electric signal depending upon the intensity thereof.

Figure 2:
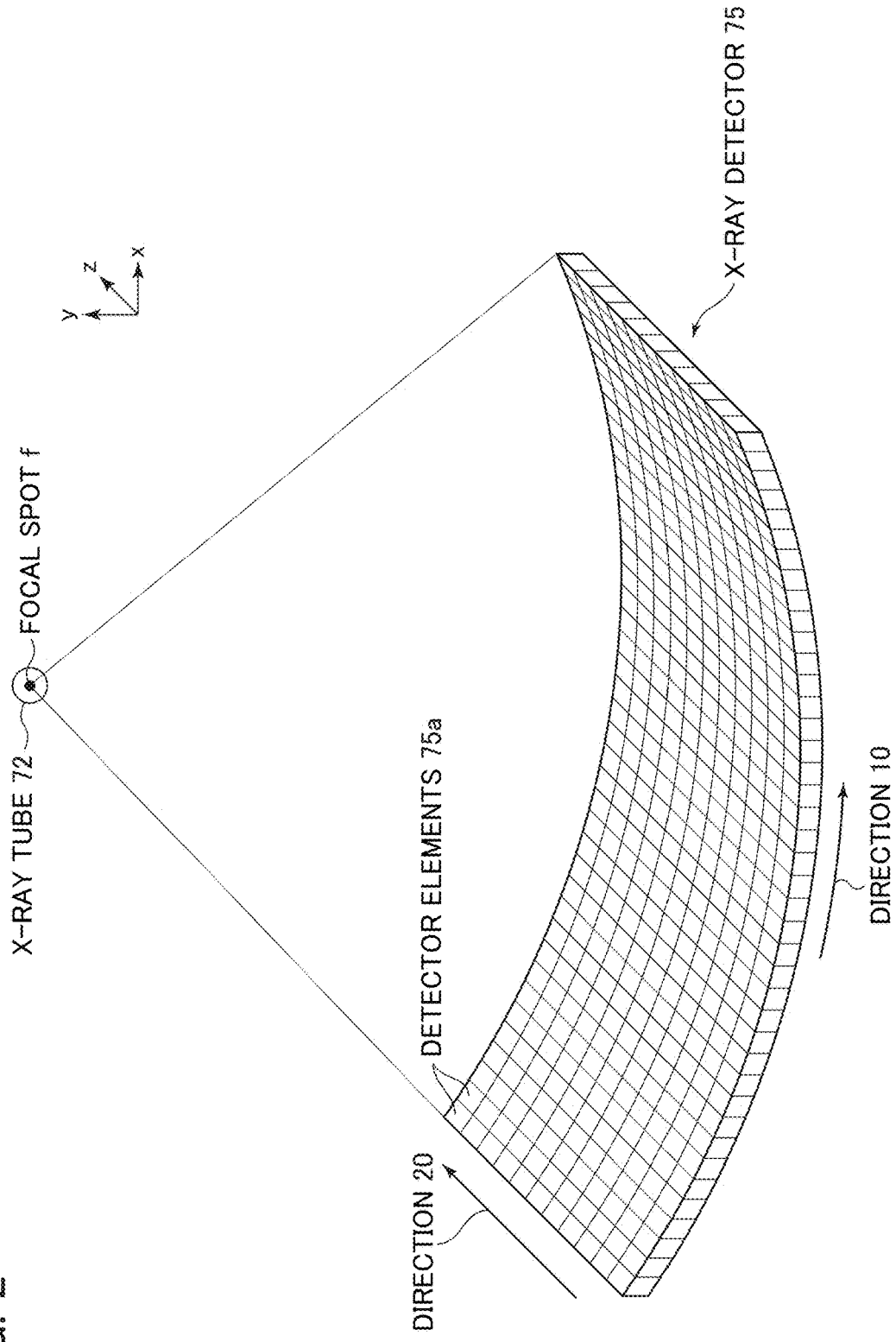
FIG. 2 is a perspective view of an X-ray detector 75.
Figure 3:
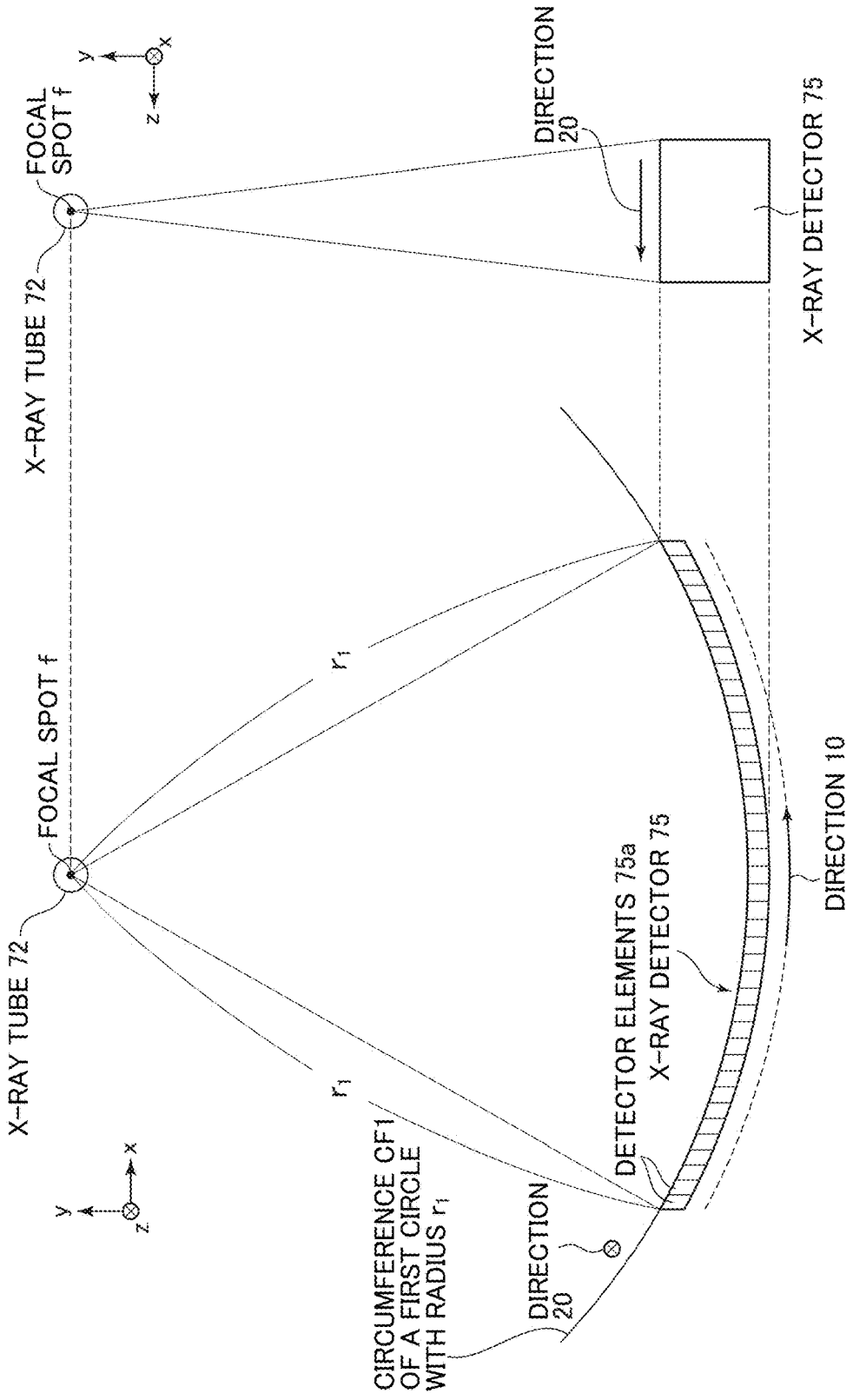
FIG. 3 is a view (left) of the X-ray detector 75 in a body-axis direction (z-direction), and a view (right) of the X-ray detector 75 in an x-direction.

FIGS. 2 and 3 are explanatory diagrams for the X-ray detector 75.

FIG. 2 is a perspective view of the X-ray detector 75, and FIG. 3 is a view (left) of the X-ray detector 75 in a body-axis direction (z-direction), and a view (right) of the X-ray detector 75 in an x-direction.

The X-ray detector 75 comprises a plurality of detector elements 75a. The plurality of detector elements 75a are arranged side by side in a direction 10 and in a direction 20, wherein the direction 10 is along a circumference CF1 of a first circle with radius r1 around a focal spot f in an XY-plane perpendicular to the body-axis direction (z-direction), and the direction 20 is parallel to the body-axis direction (z-direction), as shown in FIG. 3.

Returning to FIG. 1, the description will be continued.

The data collecting section 76 receives electric signals output from the respective X-ray detector elements 75a in the X-ray detector 75, and converts them into X-ray data for collection.

The imaging table 81 comprises a cradle 82 and a driving apparatus 83. The subject SU is laid on the cradle 82. The driving apparatus 83 drives the cradle 82 to move up and down in a y-direction, and moreover drives it to move in the z-direction.

The high-voltage power source 78 supplies high voltage and electric current to the X-ray tube 72.

The collimator driving apparatus 79 drives the first collimator 73 to modify the shape of its opening.

The rotation driving apparatus 80 rotationally drives the rotating section 77.

The control section 84 controls several apparatuses/sections in the gantry 71, the driving apparatus 83, and others.

The operation console 9 accepts several kinds of operations from an operator. The operation console 9 comprises an input device 91, a display device 92, a storage device 93, and a computational processing device 94. In the present embodiment, the operation console 9 is constructed from a computer.

As used herein, the direction of the body axis of the subject SU, i.e., a direction of transportation of the subject SU by the imaging table 81, will be referred to as z-direction, as shown in FIG. 1. The vertical direction will be referred to as y-direction, and the horizontal direction orthogonal to the y- and z-directions will be referred to as x-direction.

A characteristic feature of the CT apparatus in the first embodiment is the first collimator. In the first embodiment, the collimator 73 is configured to have a structure suitable for beam tracking techniques for reducing a subject's radiation exposure. Now the collimator 73 in the first embodiment will be described. In the following description, to facilitate the understanding of the structure of the collimator 73 in the first embodiment, a collimator having a structure different from the collimator 73 in the first embodiment will be described first (which will be referred to as "collimator in a comparative example"). The collimator 73 in the first embodiment will be described after describing the collimator in the comparative example.

Figure 4:
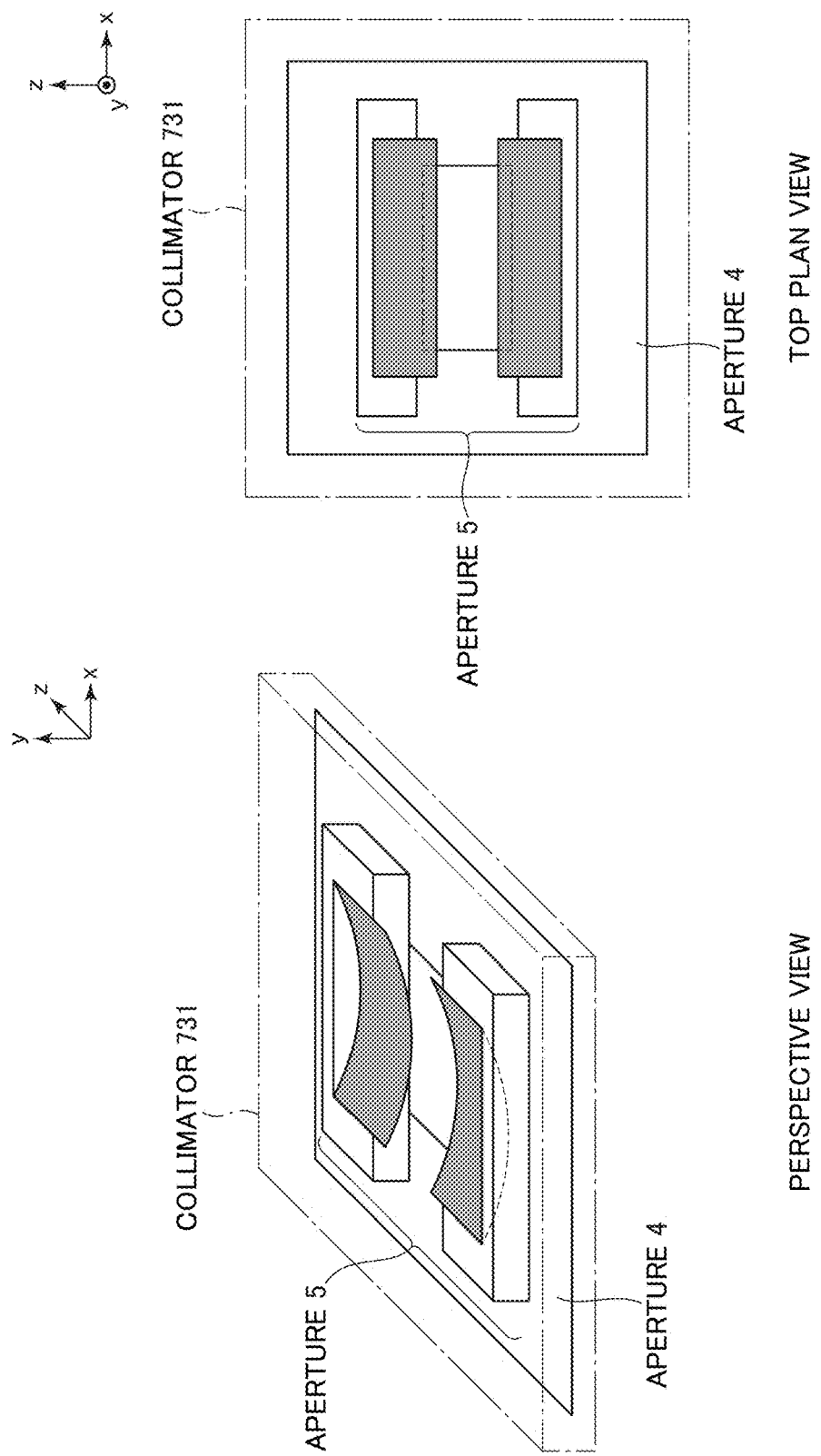
FIG. 4 is a perspective view and a top plan view showing a main portion of a collimator 731 in a comparative example.

FIGS. 4 and 5 are explanatory diagrams for the collimator 731 in the comparative example.

FIG. 4 is a perspective view and a top plan view showing the main portion of the collimator 731 in the comparative example, and FIG. 5 is a perspective view of apertures, which are the main portion of the collimator 731.

The collimator 731 has an aperture 4 and an aperture 5 for shaping an X-ray beam. The aperture 5 is placed above the aperture 4. While the collimator 731 also comprises a filter and the like, they are not shown, and only the apertures 4 and 5, which are important members in the description of the first embodiment, are shown.

Now the aperture 4 and aperture 5 will be described one by one.

Figure 6:
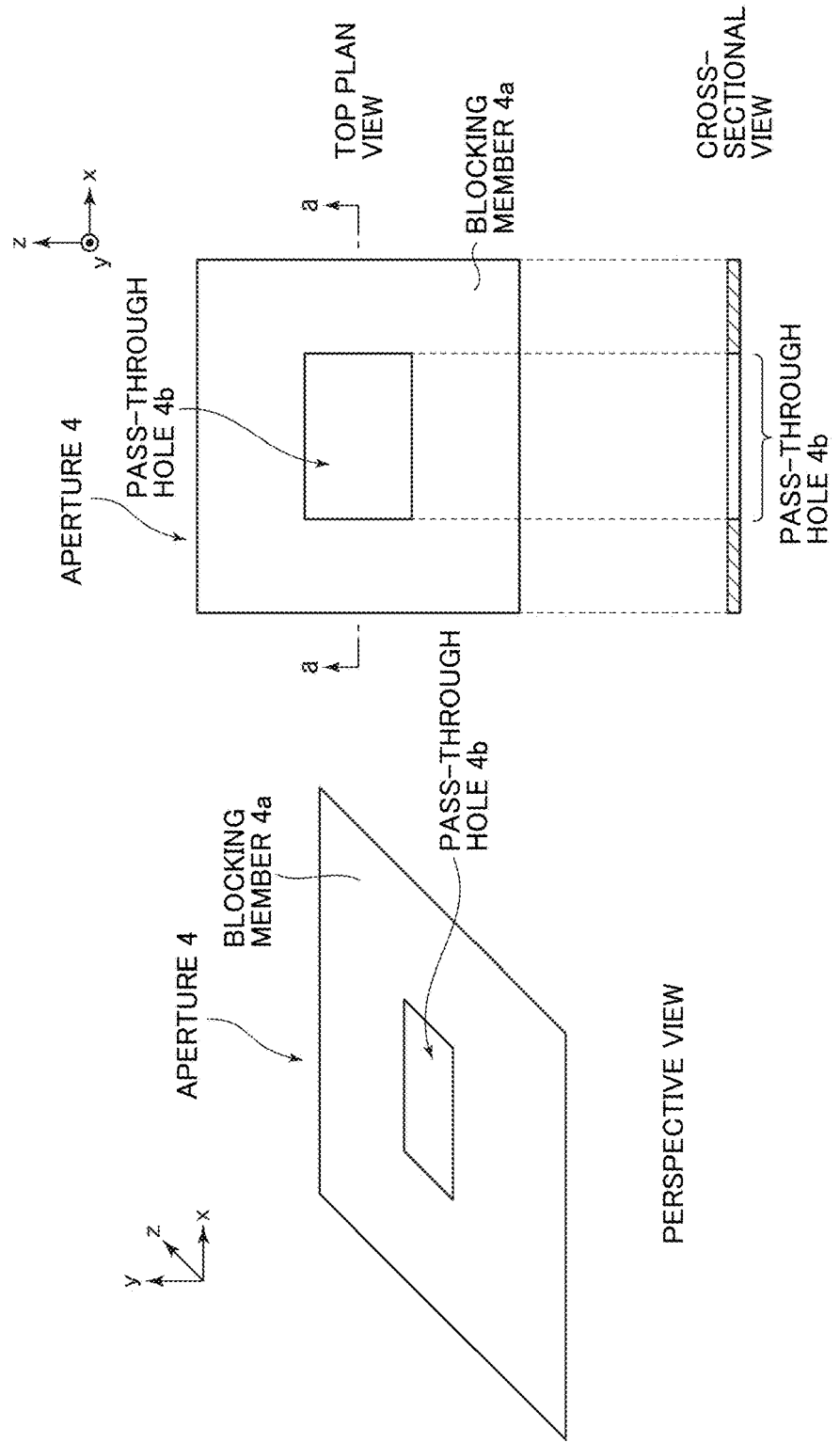
FIG. 6 is an explanatory diagram for an aperture 4.

FIG. 6 is an explanatory diagram for the aperture 4.

FIG. 6 is a drawing showing a perspective view, a top plan view, and an a-a cross-sectional view of the aperture 4.

The aperture 4 has a blocking member 4a comprising a material (for example, tungsten-containing material) for blocking X-rays. The blocking member 4a also has a pass-through hole 4b for allowing X-rays to pass through. The aperture 4 moreover has a supporting member (not shown) for supporting the blocking member 4a.

Figure 7:
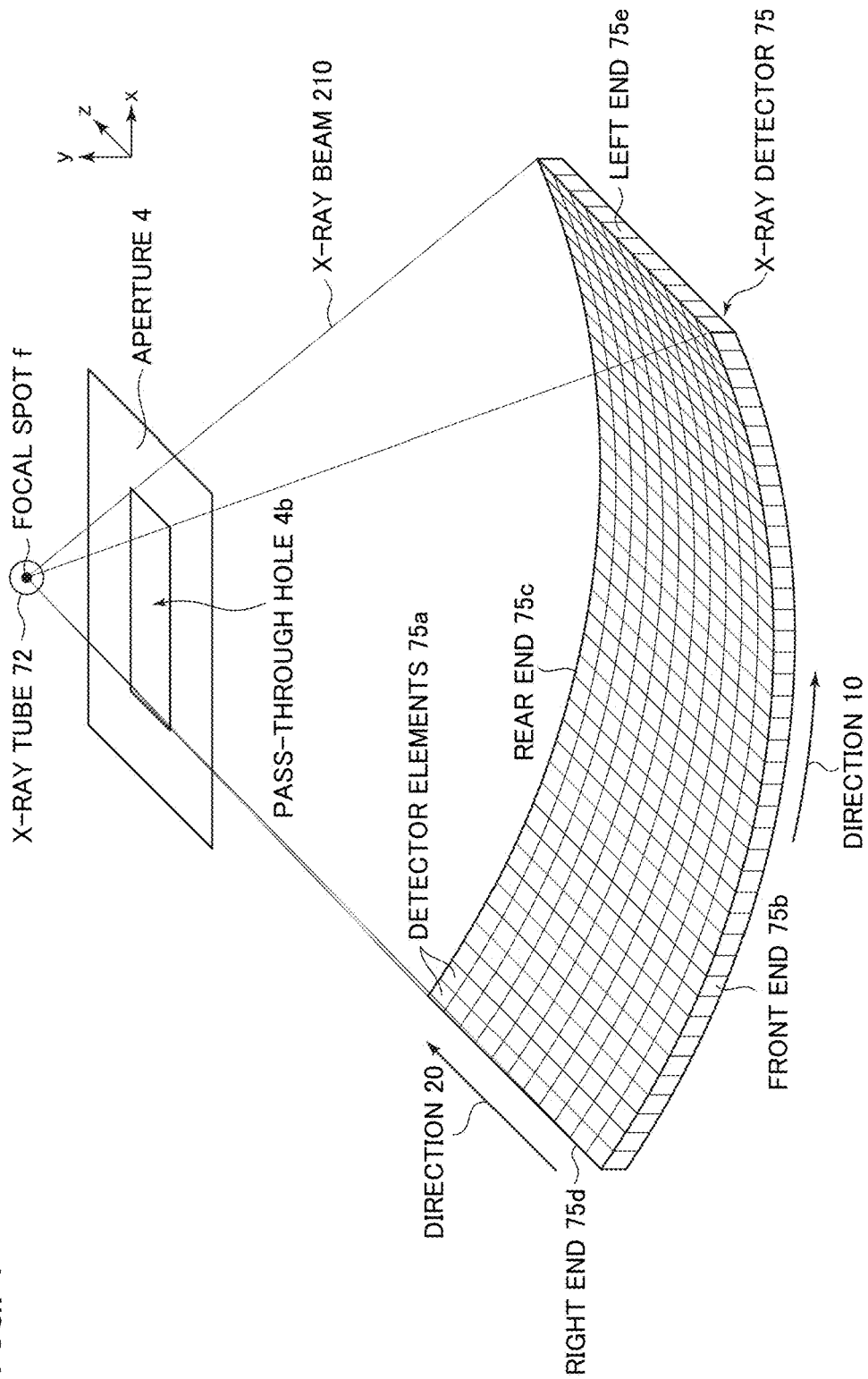
FIG. 7 is a perspective view of the aperture 4 and X-ray detector 75.
Figure 8:
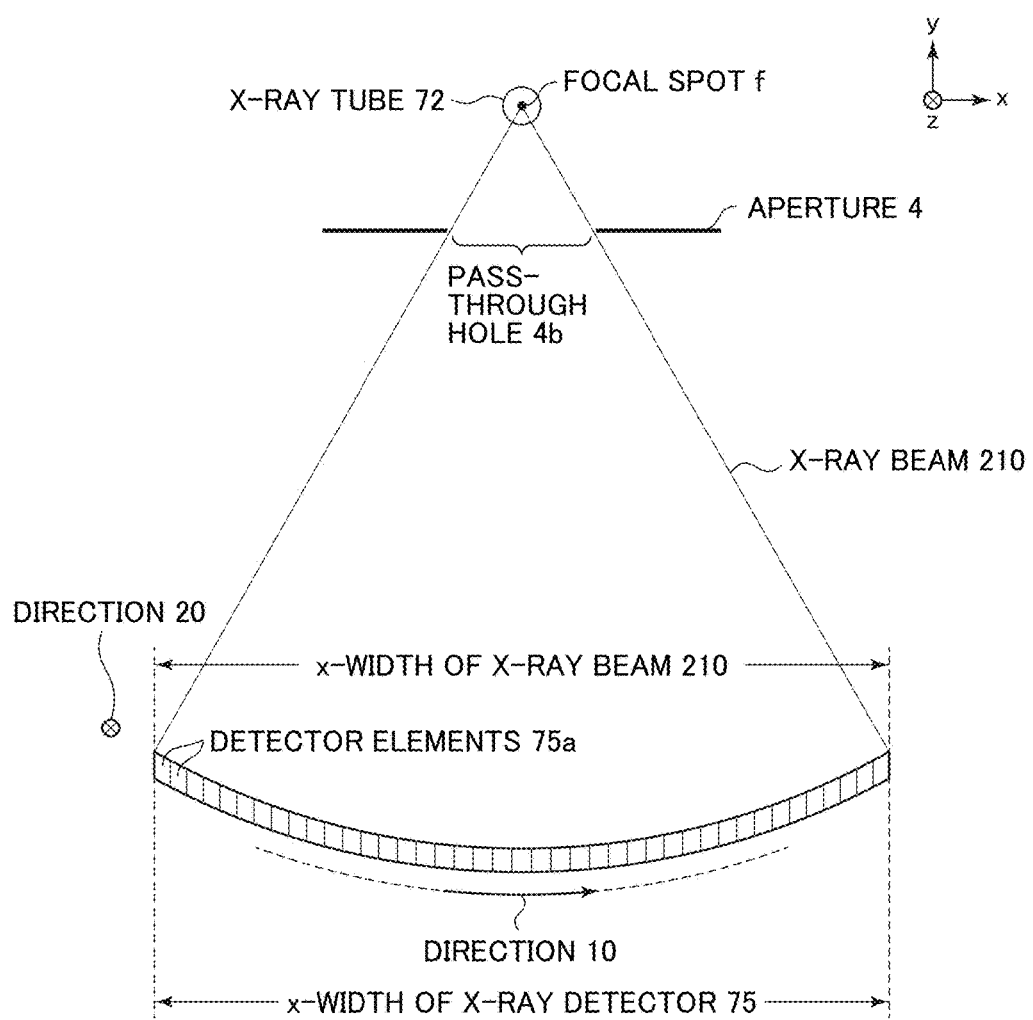
FIG. 8 is a view of the aperture 4 and X-ray detector 75 in the body-axis direction (z-direction)

FIGS. 7 and 8 are diagrams showing a positional relationship between the aperture 4 and X-ray detector 75.

FIG. 7 is a perspective view of the aperture 4 and X-ray detector 75, and FIG. 8 is a view of the aperture 4 and X-ray detector 75 in the body-axis direction (z-direction).

The aperture 4 is a member for defining the beam extent on the X-ray detector 75 in the x-direction (direction 10). Of the X-ray beam 210 emitted from the X-ray tube, X-rays passing through the pass-through hole 4b in the aperture 4 reach the X-ray detector 75, while those impinging upon the aperture 4 are blocked, whereby the x-extent of the X-ray beam 210 may be defined. The pass-through hole 4b in the aperture 4 is formed so that the beam x-width of the X-ray beam 210 almost matches the x-width of the X-ray detector 75 (a width between a left end 75e and a right end 75d of the X-ray detector 75).

On the other hand, the z-extent of the X-ray beam 210 is defined by the other aperture 5, rather than the aperture 4, placed above the aperture 4. Now the aperture 5 will be described.

Figure 9:
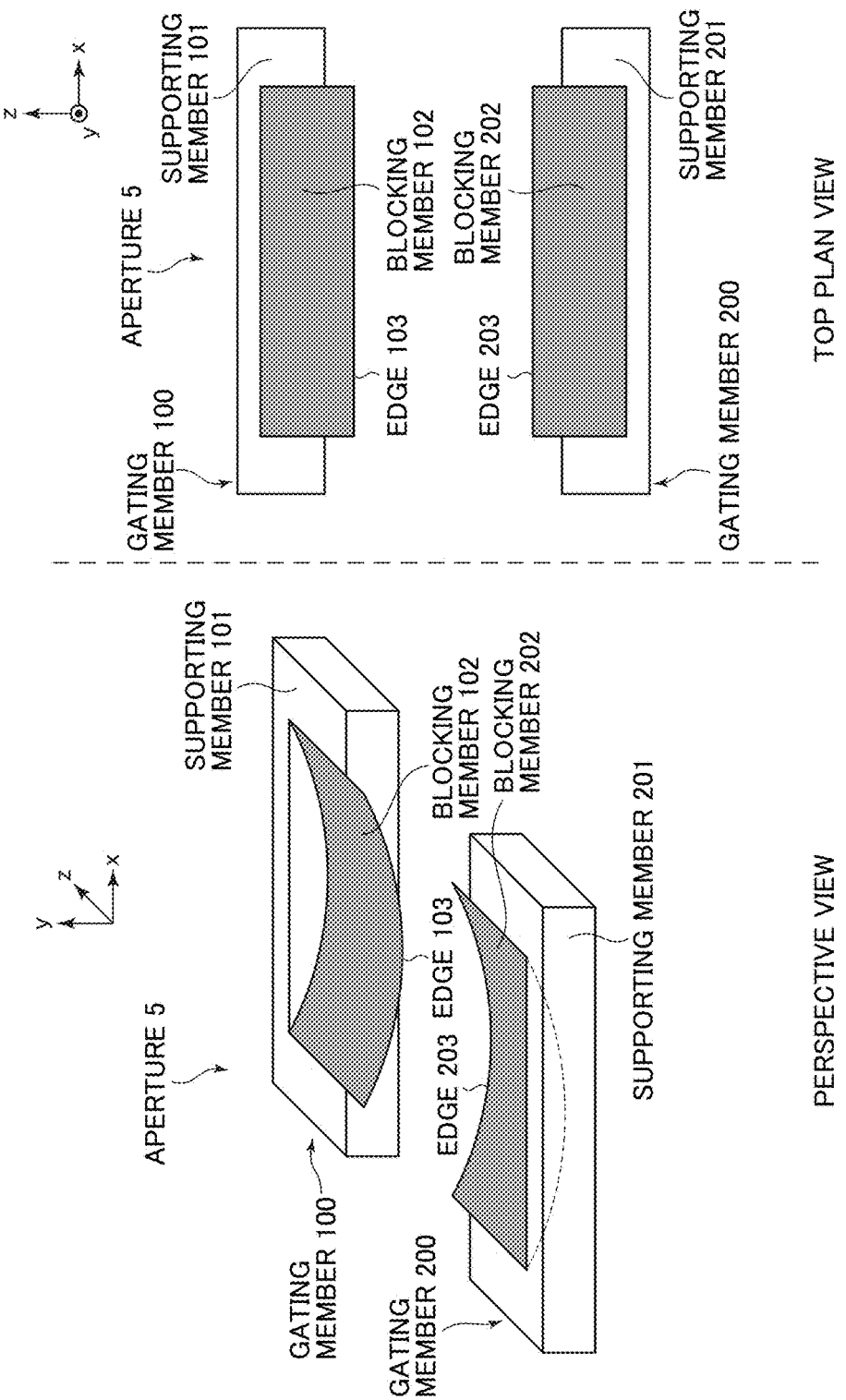
FIG. 9 is an explanatory diagram for an aperture 5.

FIG. 9 is an explanatory diagram for the aperture 5.

In FIG. 9 are shown a perspective view (left) and a top plan view (right) of the aperture 5.

The aperture 5 comprises two gating members 100 and 200.

The gating member 100 comprises a blocking member 102 for blocking X-rays, and a supporting member 101 for supporting the blocking member 102; the gating member 200 comprises a blocking member 202 for blocking X-rays, and a supporting member 201 for supporting the blocking member 202.

In the aperture 5 as viewed from above, the supporting member 101 supports the blocking member 102 so that an edge 103 of the blocking member 102 protrudes from the supporting member 101, while the supporting member 201 supports the blocking member 202 so that an edge 203 of the blocking member 202 protrudes from the supporting member 201.

Figure 10:
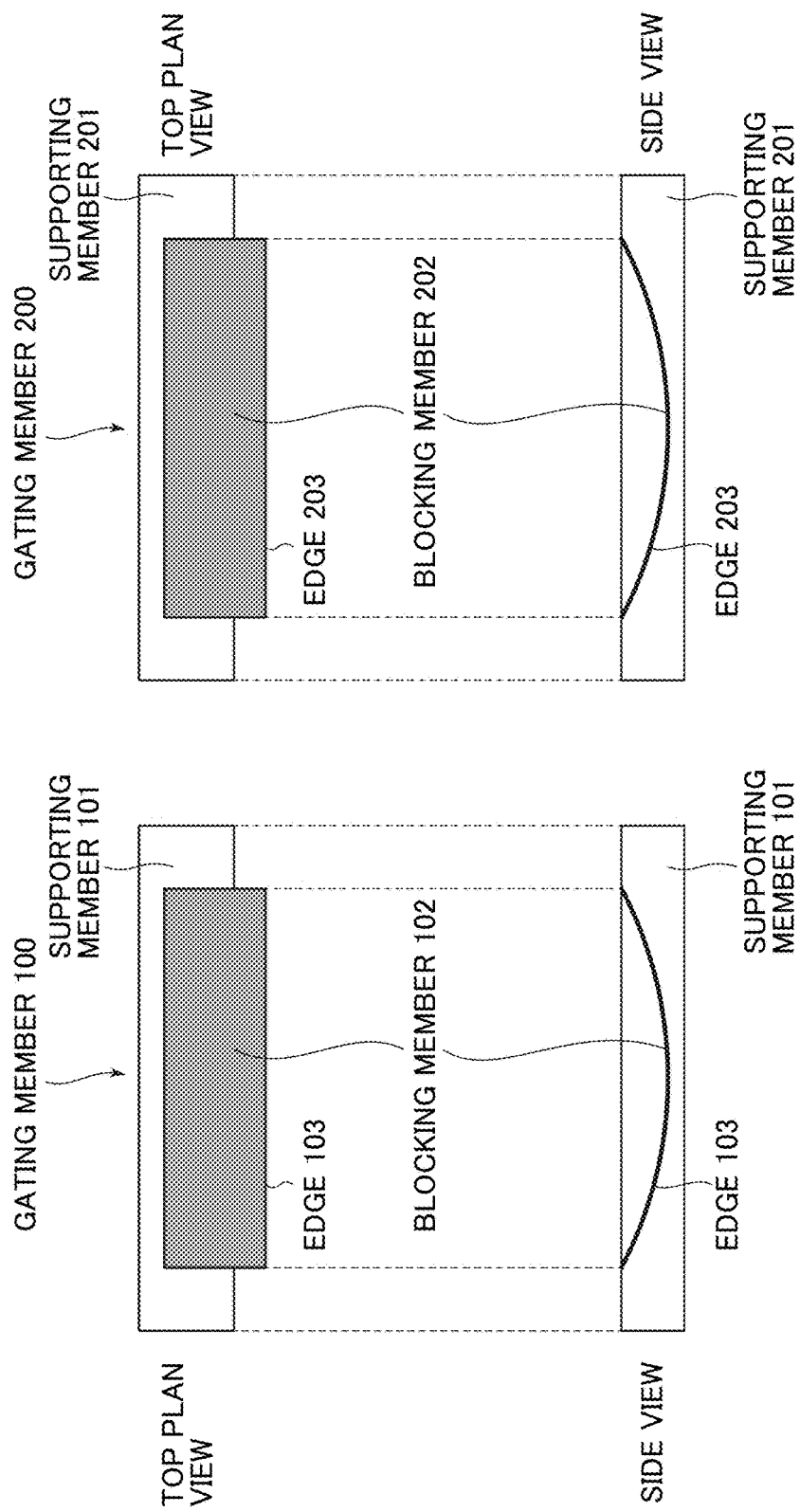
FIG. 10 is a top plan view and a side view of each of gating members 100 and 200.

FIG. 10 is a top plan view and a side view of each of the gating members 100 and 200.

In FIG. 10, to facilitate the comparison of the gating members 100 and 200, the top plan views and side views of the gating members 100 and 200 are shown so that the orientation of the edge 203 of the gating member 200 matches that of the edge 103 of the gating member 100.

As shown in the side views, the edge 103 of the blocking member 102 and the edge 203 of the blocking member 202 are curvilinearly formed.

The shape of the edge 103 of the blocking member 102 and that of the edge 203 of the blocking member 202 are defined based on the shape of the X-ray detector 75. Now how the shapes of the edge 103 of the blocking member 102 and the edge 203 of the blocking member 202 are defined will be particularly described referring to FIGS. 11 to 15.

Figure 11:
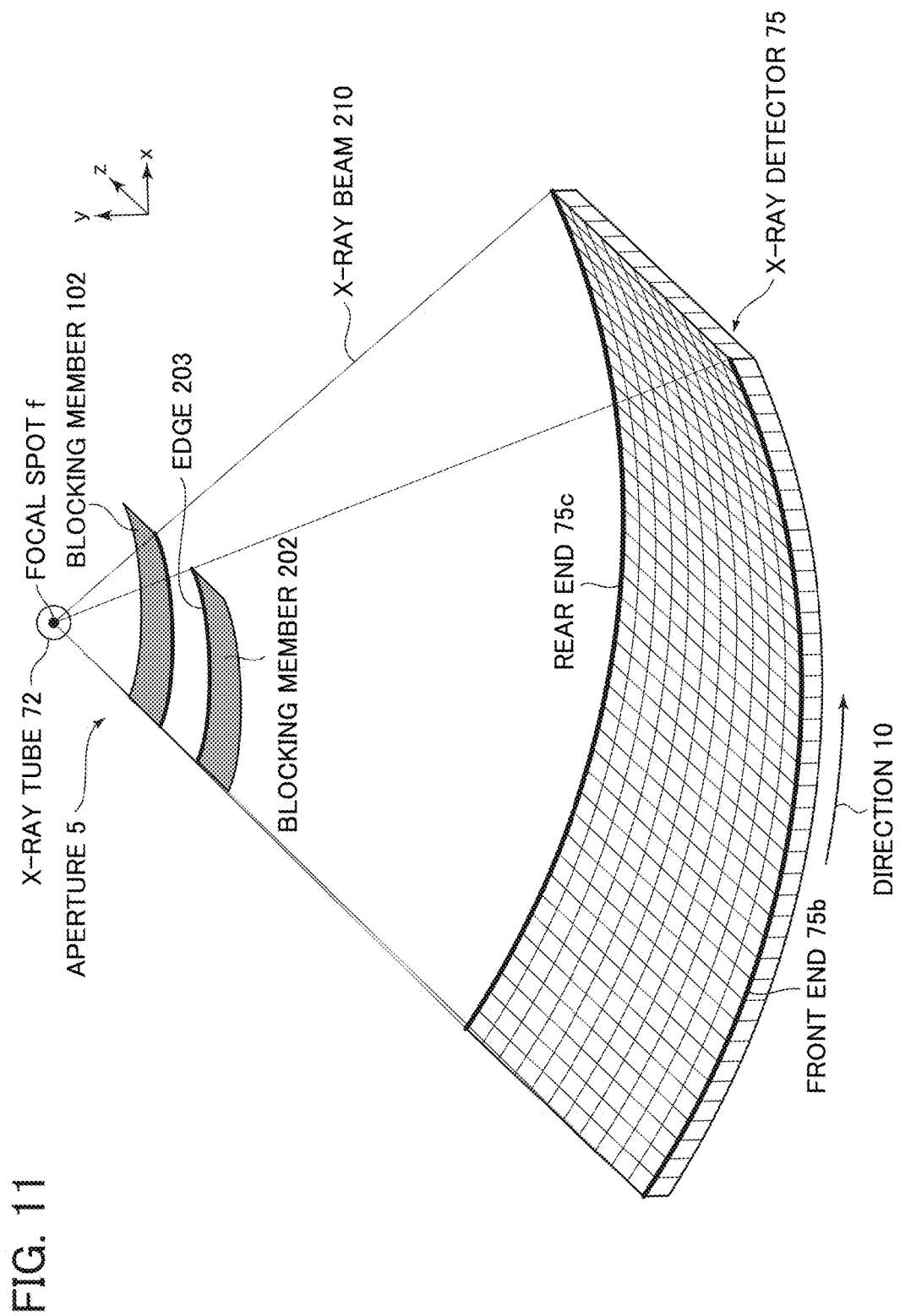
FIG. 11 is a perspective view of the aperture 5 and X-ray detector 75.
Figure 12:
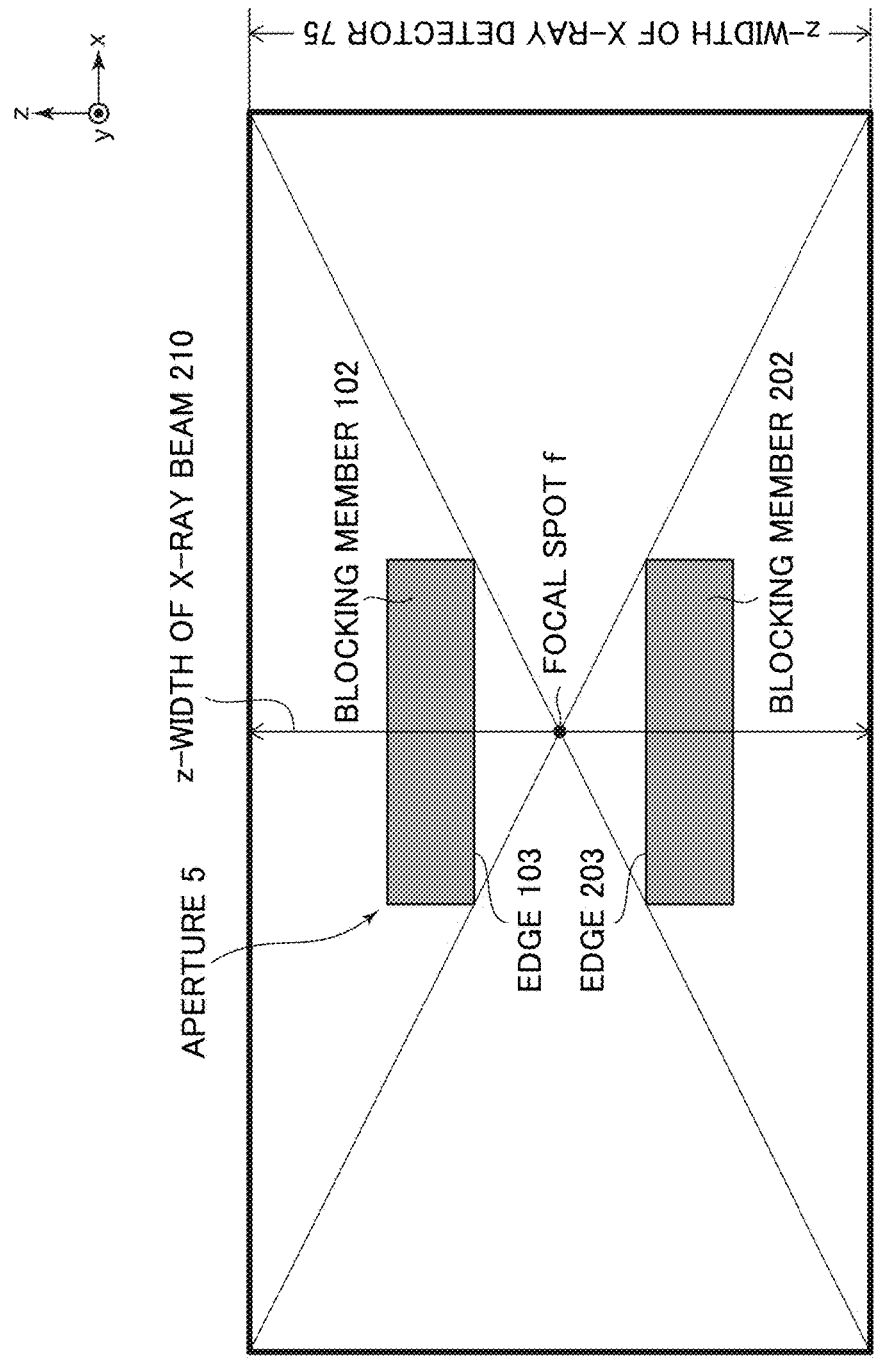
FIG. 12 is a plan view of the aperture 5 and X-ray detector 75 as viewed from a focal spot f.

FIG. 11 is a perspective view of the aperture 5 and X-ray detector 75, and FIG. 12 is a plan view of the aperture 5 and X-ray detector 75 as viewed from the focal spot f. In FIGS. 11 and 12, for the aperture 5, only the blocking members 102 and 202 are shown and the supporting members 101 and 202 are not shown for convenience of explanation.

The blocking members 102 and 202 are disposed opposite to each other in the body-axis direction (z-direction).

Figure 13:
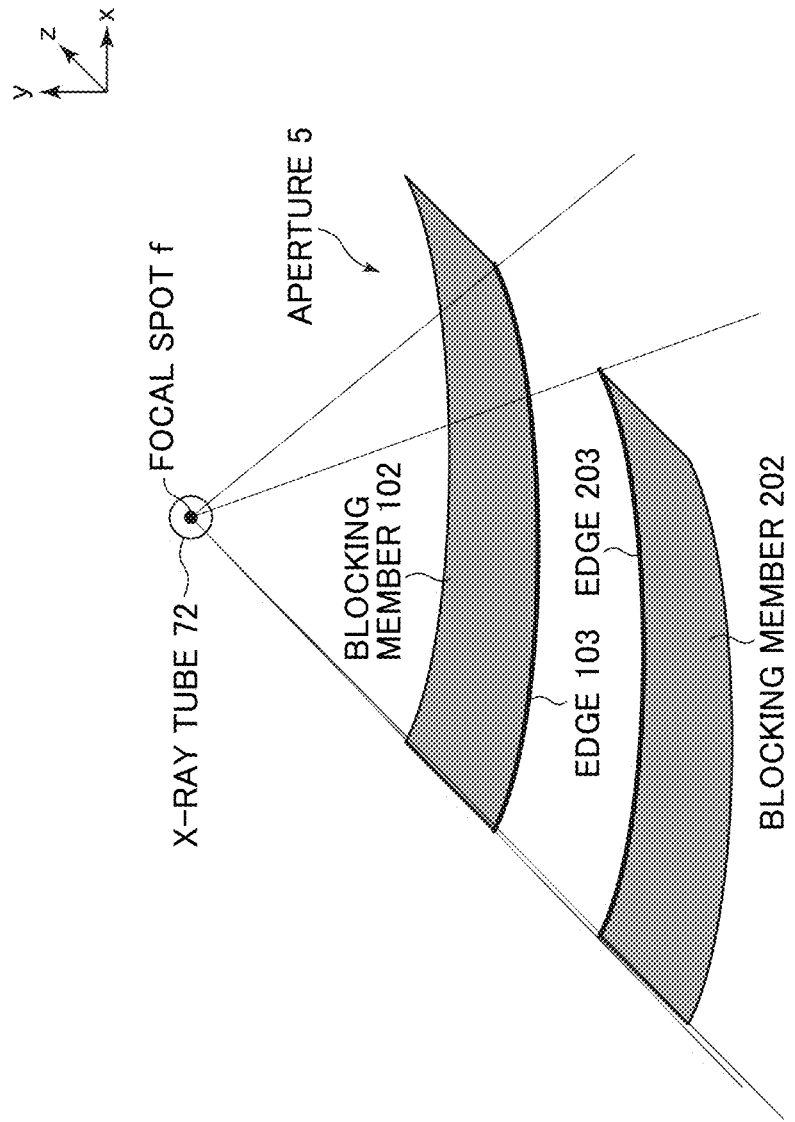
FIG. 13 is an enlarged perspective view of blocking members 102 and 202 in FIG. 11.
Figure 14:
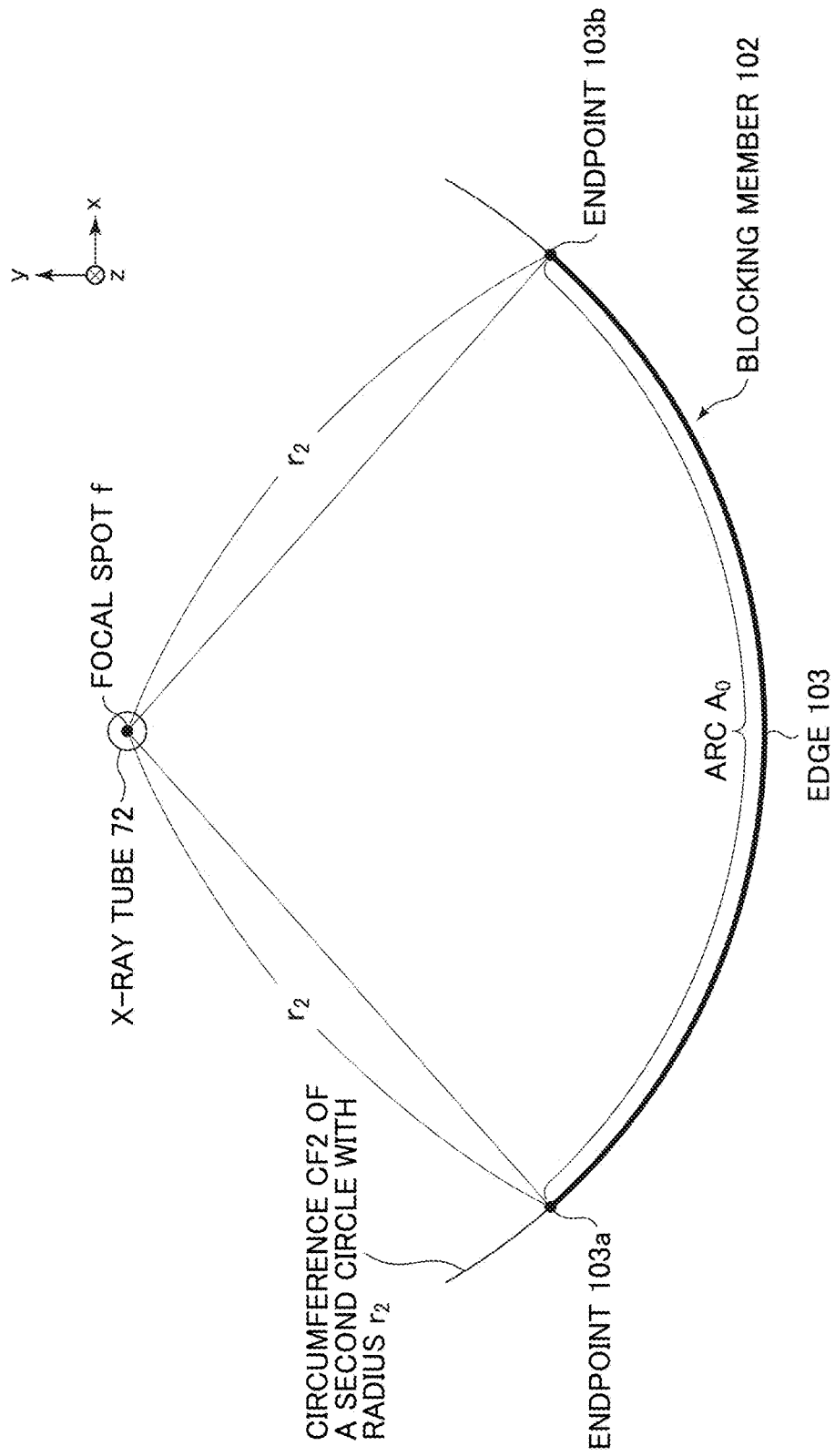
FIG. 14 is a diagram showing the shape of an edge 103 of the blocking member 102 in an XY-plane.
Figure 15:
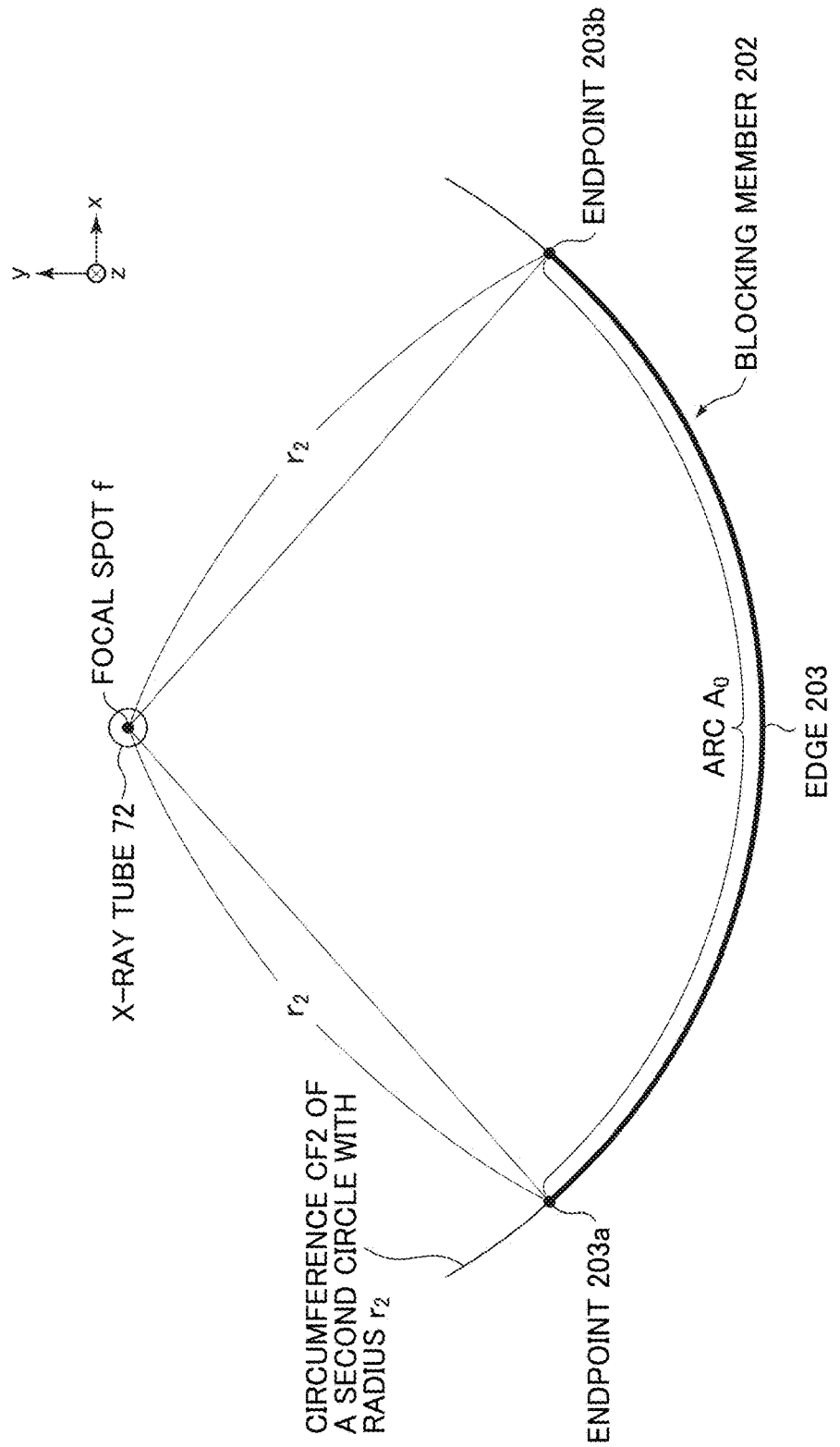
FIG. 15 is a diagram showing the shape of an edge 203 of the blocking member 202 in the XY-plane.

FIG. 13 is an enlarged perspective view of the blocking members 102 and 202 in FIG. 11, FIG. 14 is a diagram showing the shape of the edge 103 of the blocking member 102 in an XY-plane, and FIG. 15 is a diagram showing the shape of the edge 203 of the blocking member 202 in the XY-plane.

As shown in FIG. 14, the edge 103 of the blocking member 102 is formed on an arc A0 lying on a circumference CF2 of a second circle with radius r2 around the focal spot f in the XY-plane. The edge 103 of the blocking member 102 has two endpoints 103a and 103b, and is formed to extend on the arc A0 from the endpoint 103a toward the endpoint 103b in the XY-plane, as shown in FIG. 14.

On the other hand, the edge 203 of the blocking member 202 is shown in FIG. 15.

Similarly to the edge 103 of the blocking member 102, the edge 203 of the blocking member 202 is formed on the arc A0 lying on the circumference CF2 of the second circle with radius r2 around the focal spot f in the XY-plane. The edge 203 of the blocking member 202 has two endpoints 203a and 203b, and is formed to extend on the arc A0 from the endpoint 203a toward the endpoint 203b in the XY-plane, as shown in FIG. 15.

Moreover, the edge 103 of the blocking member 102 and the edge 203 of the blocking member 202 are formed in parallel with each other in the ZX-plane, as shown in FIG. 12.

Of the X-ray beam 210, X-rays traveling toward a region sandwiched between the edge 103 of the blocking member 102 and the edge 203 of the blocking member 202 reach the X-ray detector 75, while those impinging upon the blocking members 102 and 202 are blocked, whereby the z-extent of the X-ray beam 210 may be limited. In FIG. 12 is shown the X-ray beam 210 shaped to have a z-width almost matching the z-width of the X-ray detector 75.

Figure 16:
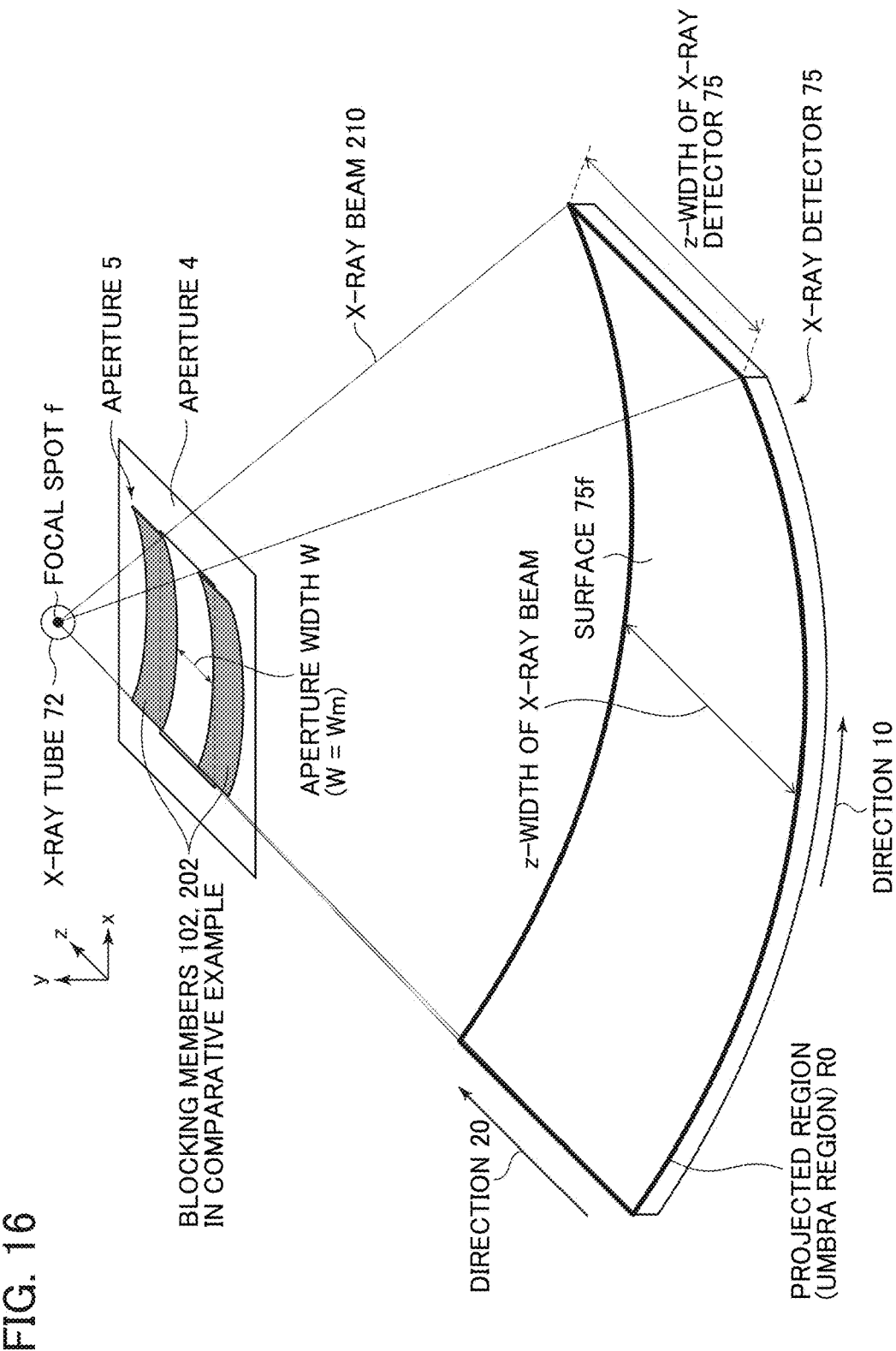
FIG. 16 is a diagram schematically showing a positional relationship between the apertures 4 and 5 and X-ray detector 75.

As described above, the aperture 4 defines the x-extent of the X-ray beam 210 (see FIG. 8), while the aperture 5 defines the z-extent of the X-ray beam 210 (see FIG. 12). Thus, the x- and z-extents of the X-ray beam 210 may be defined by the apertures 4 and 5. In FIG. 16 is schematically shown a positional relationship between both the apertures 4 and 5 and the X-ray detector 75. In FIG. 16 an aperture width W of the blocking members 102 and 202 of the aperture 5 is set to W=Wm (for example, maximum aperture width) so that the z-width of the X-ray beam 210 almost matches the z-width of the X-ray detector 75. In this case, it is by the apertures 4 and 5 that a beam-projected region R0 by the X-ray beam 210 on a surface 75f of the X-ray detector 75 can be defined to have a rectangular shape almost matching the outline of the X-ray detector 75. Thus, the X-ray beam 210 may be shaped so that its projected region R0 has an ideal rectangular shape.

However, in FIG. 16, since the projected region R0 by the X-ray beam 210 almost matches the outline of the X-ray detector 75, the whole surface 75f of the X-ray detector 75 is a region of an umbra of the X-ray beam 210. Therefore, in the case that the beam z-width of the X-ray beam 210 matches the z-width of the X-ray detector 75, the X-ray detector 75 cannot be provided on its surface 75f with a region of a penumbra of the X-ray beam 210, resulting in a problem that beam tracking cannot be applied. Accordingly, to enable beam tracking, it may be contemplated to use different blocking members as below (see FIGS. 17 and 18), in place of the blocking members 102 and 202.

Figure 17:
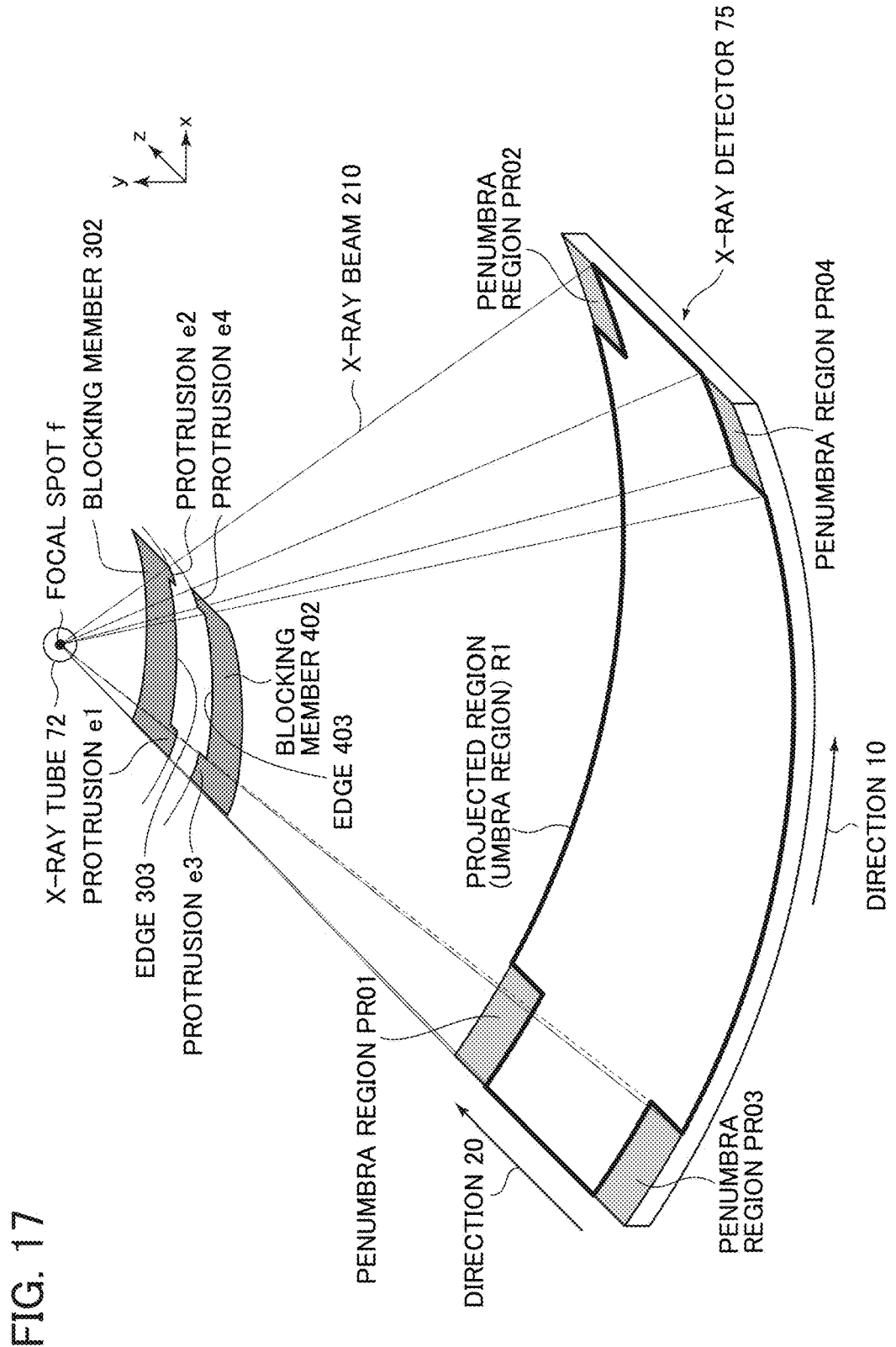
FIG. 17 is a perspective view of blocking members 302 and 402 and the X-ray detector 75.
Figure 18:
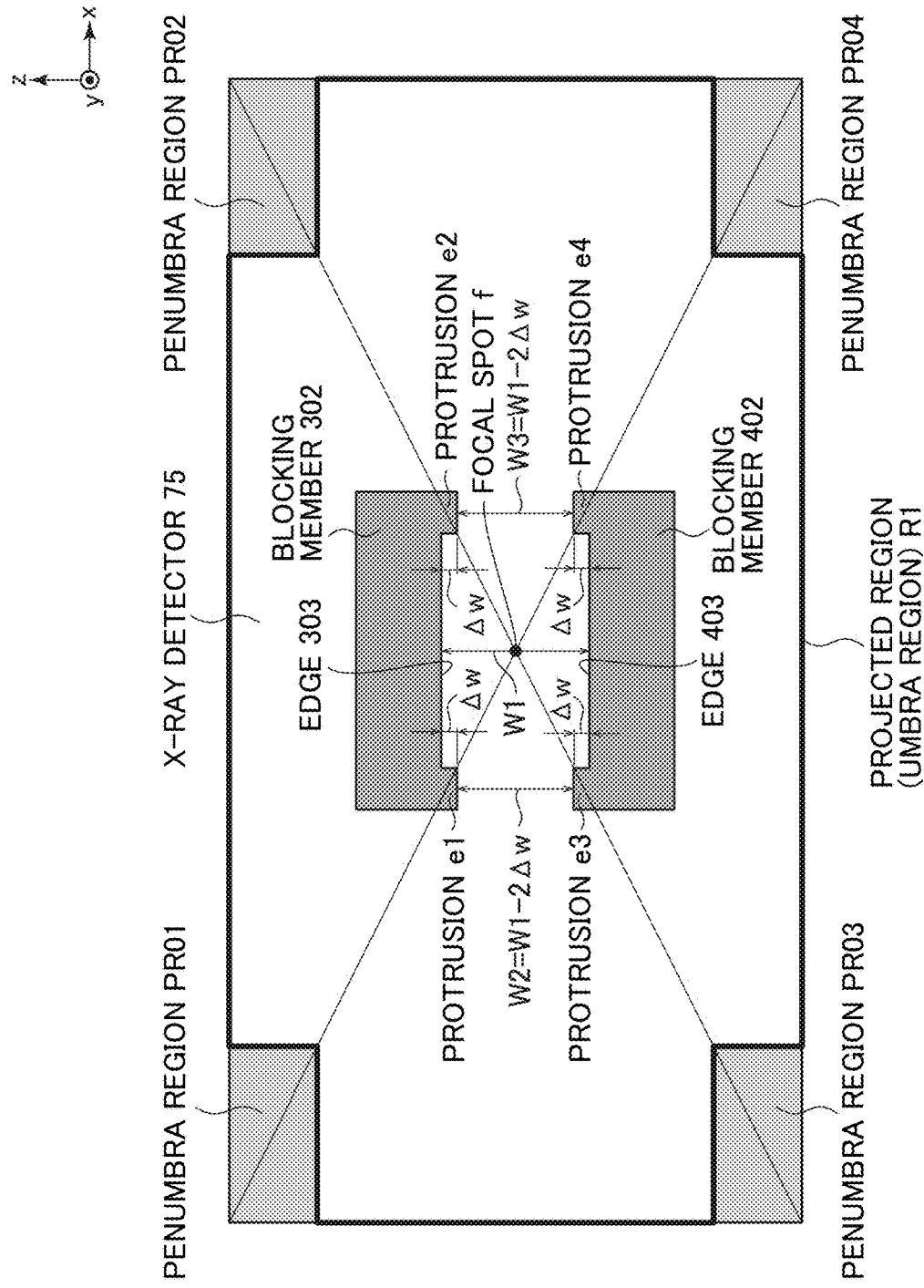
FIG. 18 is a plan view of the blocking members 302 and 402 and X-ray detector 75 as viewed from a focal spot f.

FIGS. 17 and 18 are explanatory diagrams for blocking members 302 and 402 different from the blocking members 102 and 202.

FIG. 17 is a perspective view of the blocking members 302 and 402 and X-ray detector 75, and FIG. 18 is a plan view of the blocking members 302 and 402 and X-ray detector 75 as viewed from the focal spot f. In FIGS. 17 and 18, the aperture 4 (see FIG. 7) is not shown for convenience of explanation.

The blocking member 302 has protrusions e1 and e2 protruding in a direction opposite to the z-direction at both ends of the edge 303, as shown in FIG. 18. The blocking member 402 has protrusions e3 and e4 protruding in the z-direction at both ends of the edge 403. Since the X-ray beam 210 is thus blocked by the protrusions e1 to e4, the X-ray detector 75 may be provided in its four corners with penumbra regions PR01 to PR04.

However, since it is necessary to provide the blocking members 302 and 402 with the protrusions e1 to e4, an aperture width W2 between the protrusion e1 and protrusion e3, and an aperture width W3 between the protrusion e2 and protrusion e4 are smaller than an aperture width W1 between the edge 303 and edge 403 by 2Δw. Therefore, the aperture width W1 cannot have a relationship W1<2Δw, resulting in a problem that the adjustable range of the aperture width W1 is limited.

Accordingly, in the first embodiment, an aperture is configured to enable beam tracking while preventing as much as possible the adjustable range of the aperture width W1 from being limited. Now an aperture in the first embodiment will be described.

Figure 19:
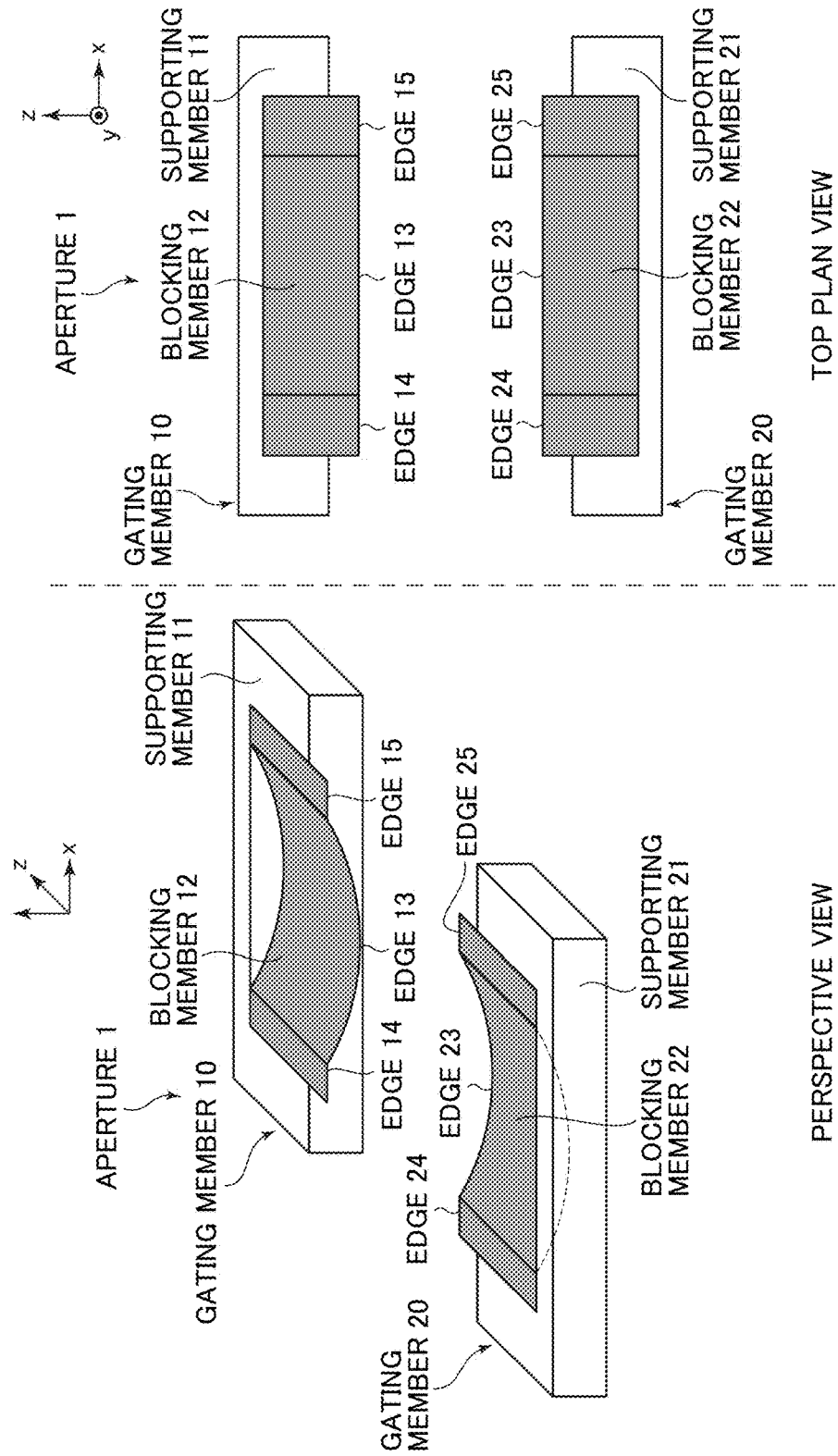
FIG. 19 is a perspective view (left) and a top plan view (right) of an aperture 1 in the first embodiment.
Figure 20:
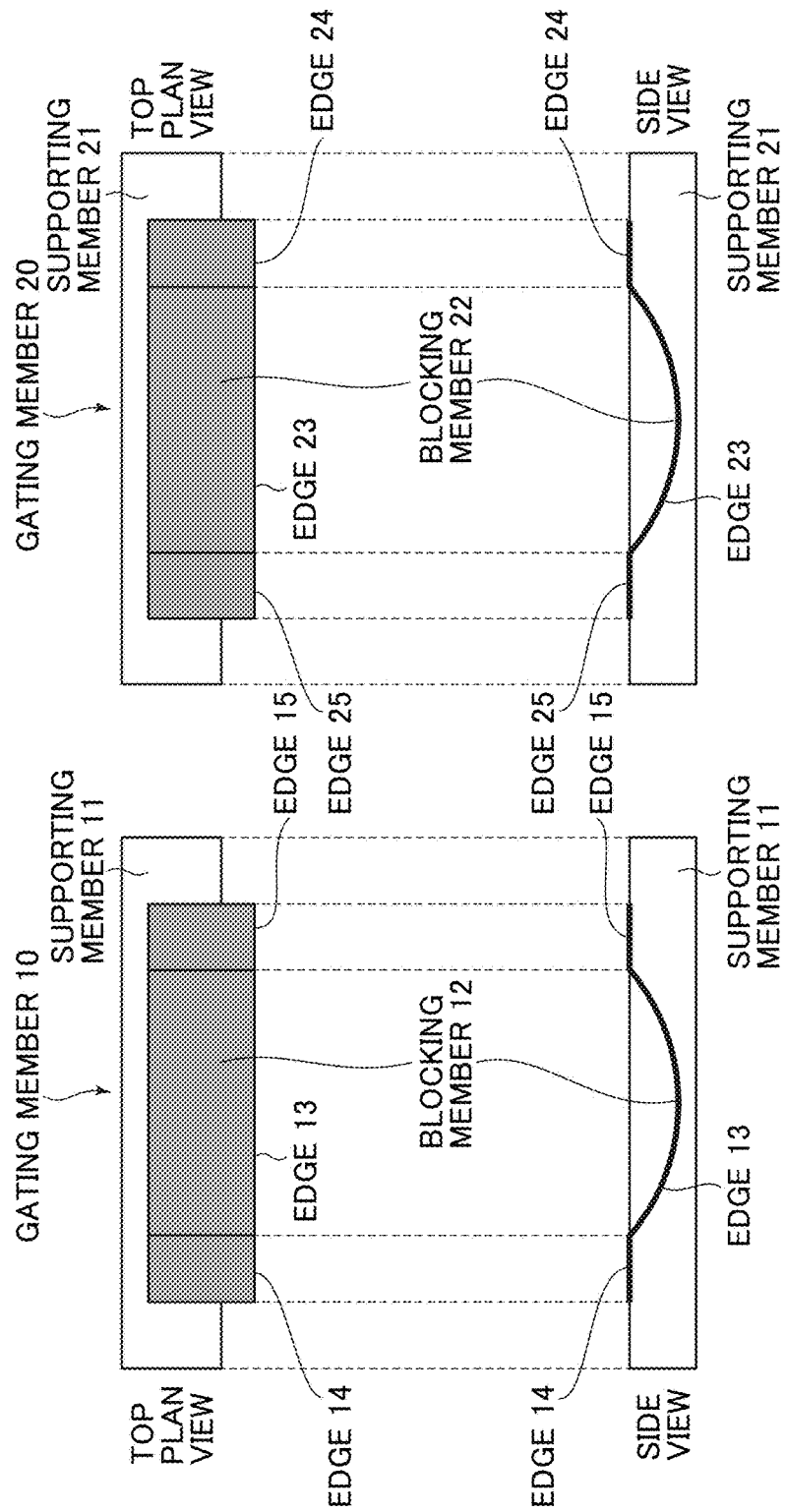
FIG. 20 is a top plan view and a side view of each gating member of the aperture 1 in the first embodiment.

FIGS. 19 and 20 are explanatory diagrams for an aperture 1 in the first embodiment.

FIG. 19 is a perspective view (left) and a top plan view (right) of the aperture 1 in the first embodiment, and FIG. 20 is a top plan view and a side view of each of gating members of the aperture 1 in the first embodiment.

The aperture 1 in the first embodiment comprises two gating members 10 and 20.

The gating member 10 comprises a blocking member 12 for blocking X-rays, and a supporting member 11 for supporting the blocking member 12; the gating member 20 comprises a blocking member 22 for blocking X-rays, and a supporting member 21 for supporting the blocking member 22.

As compared with the aperture 5 in the comparative example (see FIG. 9), the aperture 1 in the first embodiment has the blocking members 12 and 22 whose edges are different in shape. Now the shape of the edges of the blocking members 12 and 22 will be described in the first embodiment.

Figure 21:
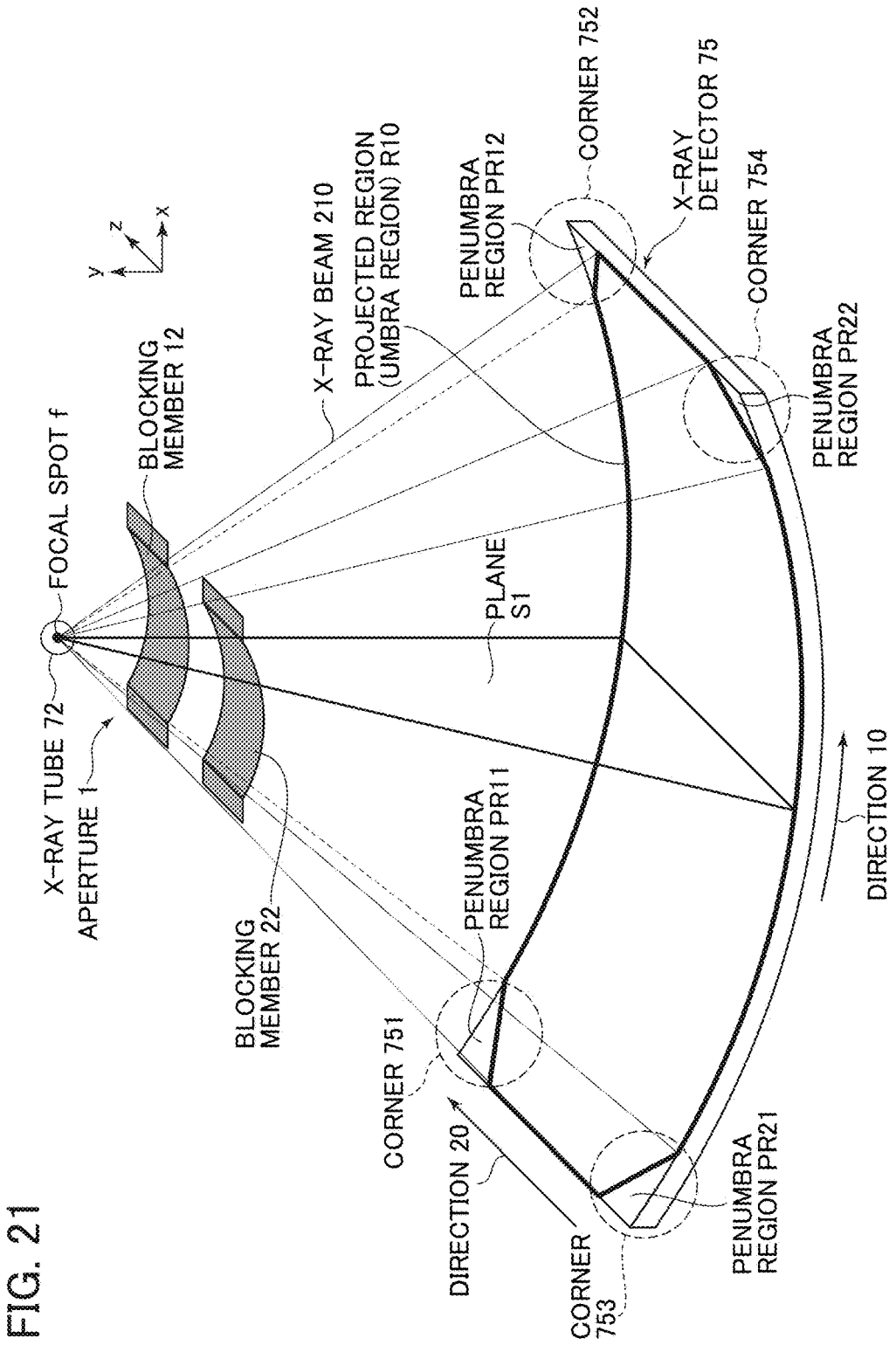
FIG. 21 is a perspective view of the aperture 1 and X-ray detector 75.
Figure 22:
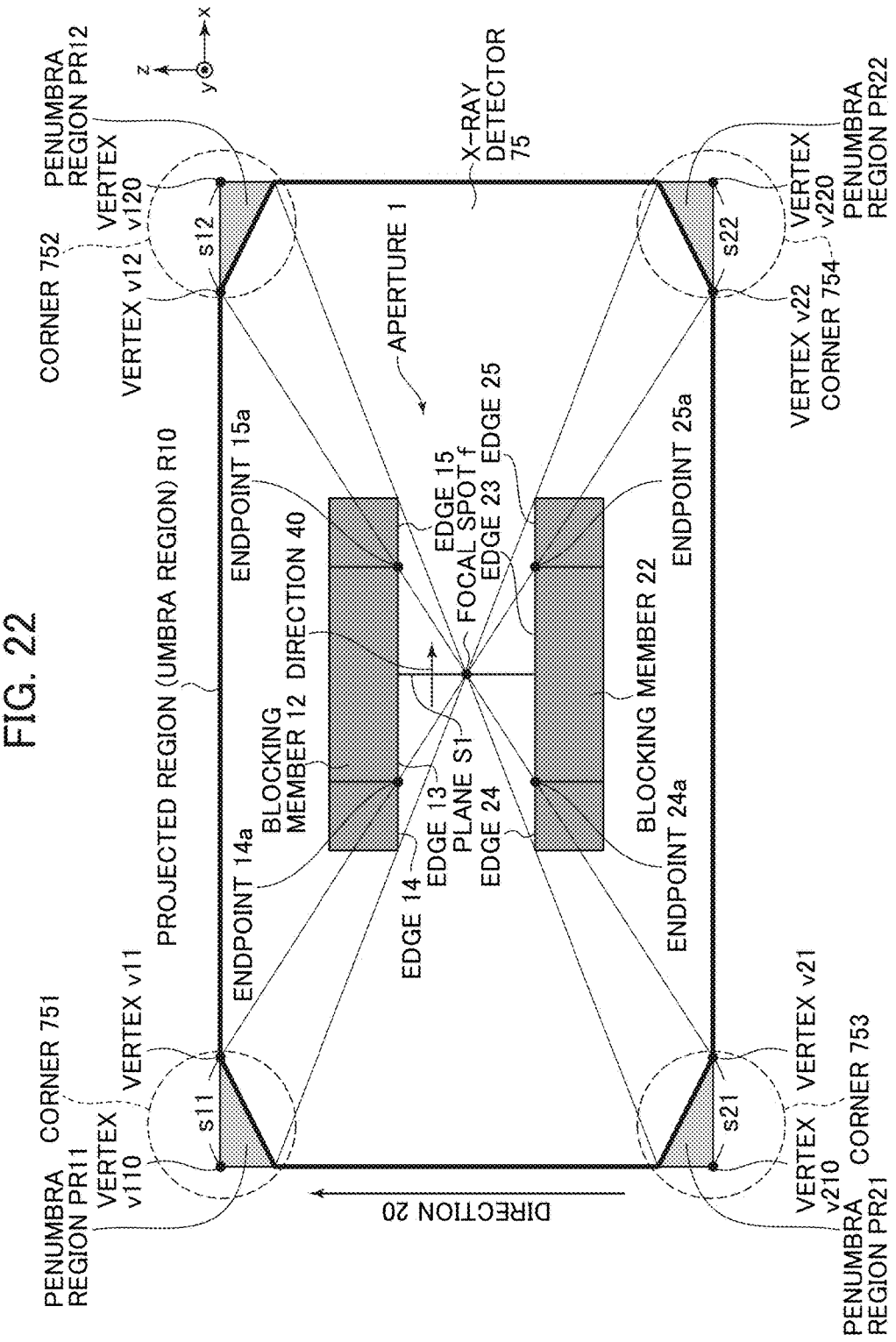
FIG. 22 is a plan view of the aperture 1 and X-ray detector 75 as viewed from a focal spot f.

FIG. 21 is a perspective view of the aperture 1 and X-ray detector 75, and FIG. 22 is a plan view of the aperture 1 and X-ray detector 75 as viewed from the focal spot f. In FIGS. 21 and 22, for the aperture 1, only the blocking members 12 and 22 are shown and the supporting members 11 and 21 are not shown for convenience of explanation.

The blocking members 12 and 22 in the aperture 1 are disposed opposite to each other in the body-axis direction (z-direction). It is by the blocking members 12 and 22 that the z-extent of the X-ray beam 210 is defined.

Now edges of the blocking members 12 and 22 will be described one by one.

Figure 23:
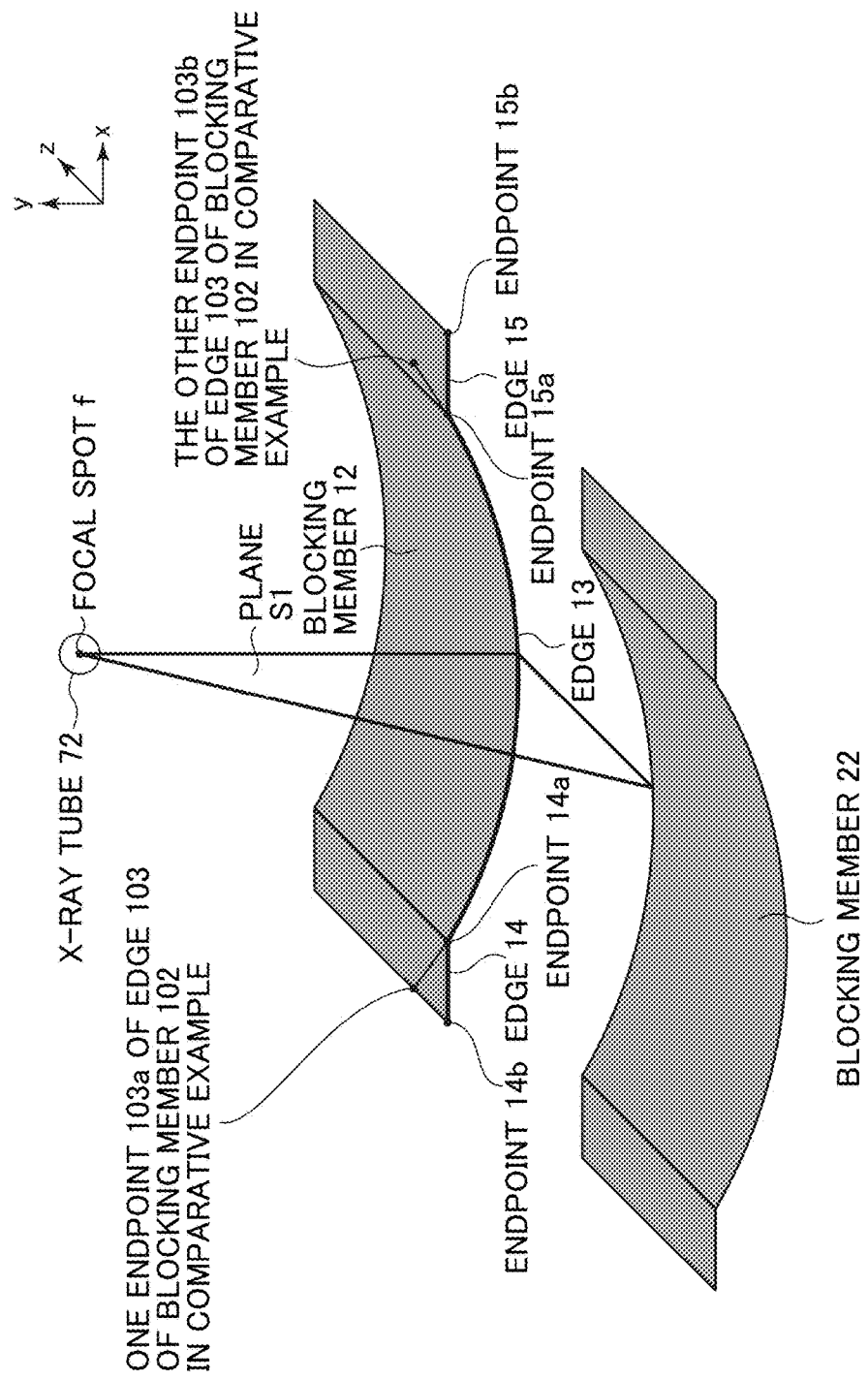
FIG. 23 is an enlarged perspective view of a blocking member 12 in FIG. 21.
Figure 24:
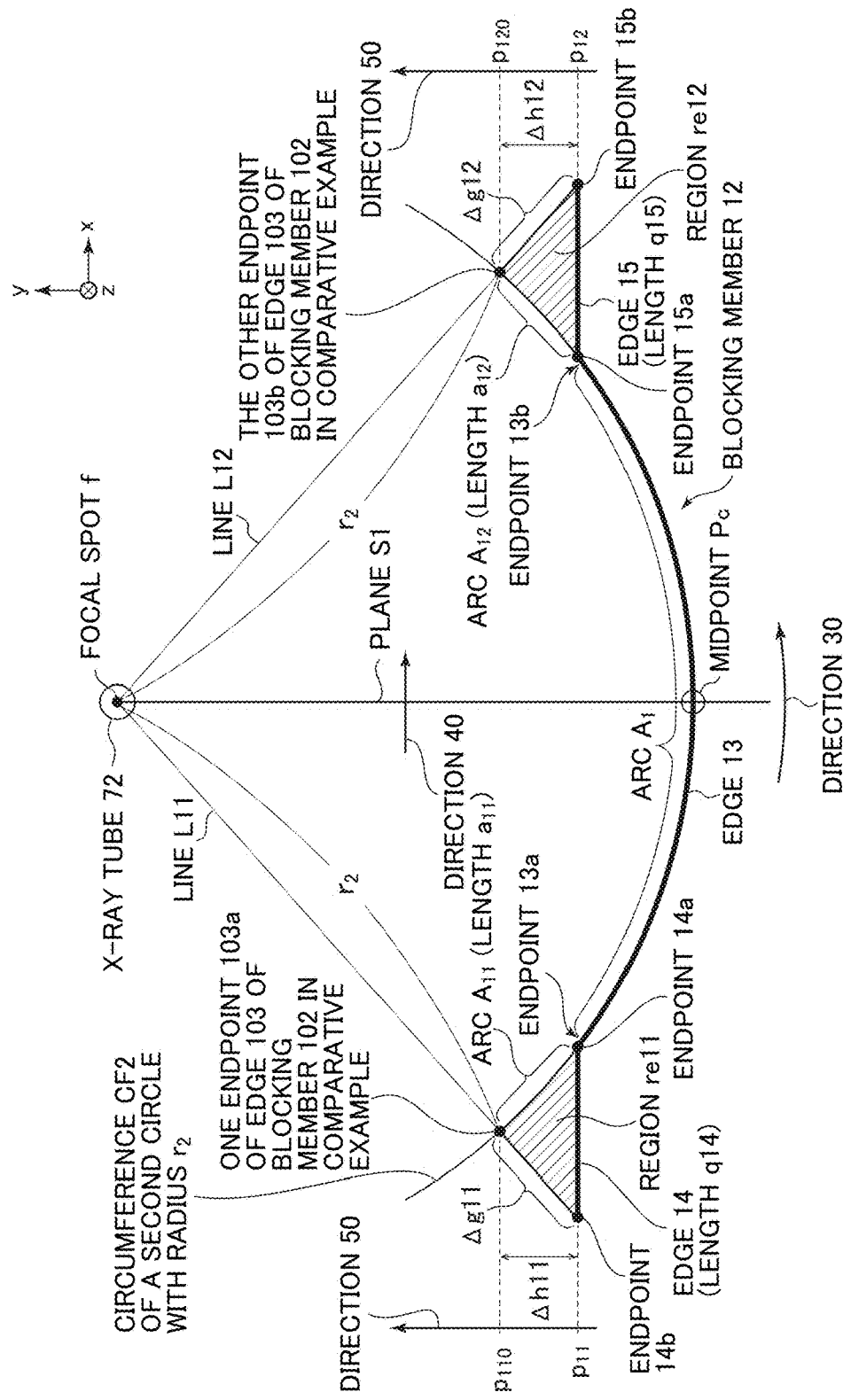
FIG. 24 is a diagram showing the shape of edges of the blocking member 12 in the XY-plane.

FIGS. 23 and 24 are explanatory diagrams for edges of the blocking member 12.

FIG. 23 is an enlarged perspective view of the blocking member 12, and FIG. 24 is a diagram showing the shape of the edges of the blocking member 12 in the XY-plane.

The blocking member 12 has an edge 13, an edge 14, and an edge 15.

As shown in FIG. 24, the edge 13 of the blocking member 12 is formed on an arc A1 lying on the circumference CF2 of the second circle with radius r2 around the focal spot f in the XY-plane. Therefore, the edge 13 of the blocking member 12 lies on the circumference CF2 of the second circle with radius r2, which is similar to the edge 103 of the blocking member 102 in the comparative example (see FIG. 14) in this regard. The edge 13 of the blocking member 12 in the first embodiment, however, is formed to be shorter than the edge 103 of the blocking member 102 in the comparative example. In FIGS. 23 and 24, the one endpoint 103a and the other endpoint 103b of the edge 103 of the blocking member 102 in the comparative example are shown to clarify the difference between the length of the edge 13 of the blocking member 12 in the first embodiment and that of the edge 103 of the blocking member 102 in the comparative example. The edge 13 of the blocking member 12 in the first embodiment is formed to be shorter than the edge 103 of the blocking member 102 in the comparative example by the total length (a11+a12) of a length a11 of an arc A11 and a length a12 of an arc A12, the arcs A11 and A12 lying on the circumference CF2 of the second circle with radius r2. While a11 and a12 are set so that a11=a12 in the first embodiment, it is possible to set them so that a11≠a12.

Moreover, the blocking member 12 in the first embodiment is formed to have two straight edges 14 and 15, in addition to the arcuate edge 13.

In FIG. 24 is shown a plane S1. The plane S1 contains a midpoint PC of the edge 13 in a direction 30 along the circumference CF2, and the focal spot f, and also is parallel to the body-axis direction (z-direction). The edges 14 and 15 lie opposite to each other with respect to the plane S1.

Now the edges 14 and 15 will be described one by one.

The edge 14 is a straight edge (with length q14) extending from one endpoint 13a of the arcuate edge 13 in a direction opposite to a direction 40 perpendicular to the plane S1. The edge 14 has one endpoint 14a connected to the endpoint 13a of the arcuate edge 13 and the other endpoint 14b lying opposite to the one endpoint 14a. When a direction 50 (corresponding to the y-direction in FIG. 24) parallel to the plane S1 and perpendicular to the direction 40 is considered, the edge 14 is formed to have positions of the endpoints 14a and 14b in the direction 50 at the same position p11.

In FIG. 24 is also shown a line L11 projected on the XY-plane. The line L11 overlies the focal spot f and the one endpoint 103a of the edge 103 of the blocking member 102 in the comparative example in the XY-plane. In the first embodiment, the endpoint 14b of the edge 14 lies at a position on the line L11 projected on the XY-plane, the position being away from the one endpoint 103a of the edge 103 of the blocking member 102 in the comparative example by Δg11 toward the X-ray detector 75.

The edge 14 is formed at the position p11 lower than a position p110 of the endpoint 103a of the edge 103 of the blocking member 102 in the comparative example in the direction 50 by Δh11. Therefore, the edge 14 is formed to lie on the side of the X-ray detector 75 relative to the arc A11 contiguous to the arc A1. In FIG. 24, a region re11 surrounded by the arc A11, line L11, and edge 14 is hatched. Since the edge 103 of the blocking member 102 in the comparative example extends on the arc A11, when the blocking member 102 in the comparative example is used, an X-ray beam traveling toward the region re11 reaches the X-ray detector 75 without being blocked by the blocking member 102 in the comparative example. However, since in the blocking member 12 in the first embodiment, the edge 14 is formed on the side of the X-ray detector 75 relative to the arc A11, when the blocking member 12 in the first embodiment is used, the X-ray beam traveling toward the region re11 may be blocked by the portion of the edge 14 of the blocking member 12. Therefore, a penumbra region PR11 may be formed in a corner 751 of the detector 75 (see FIGS. 21 and 22). The endpoint 14a of the edge 14 corresponds to a vertex v11 of the penumbra region PR11. Therefore, a side S11 of the penumbra region PR11 in the direction 40 (x direction) may be adjusted to a desired length by adjusting the position p11 of the edge 14 in the direction 50 (see FIG. 24). For example, as the position p11 of the edge 14 in the direction 50 is heightened (that is, Δh11 is shortened), the endpoint 14a of the edge 14 comes closer to the endpoint 103a of the edge 103 of the blocking member 102 in the comparative example, causing the vertex v11 of the penumbra region PR11 to come closer to a vertex v110. Thus, as the position p11 of the edge 14 in the direction 50 is heightened (that is, Δh11 is shortened), the side S11 of the penumbra region PR11 may be shortened. On the other hand, as the position p11 of the edge 14 in the direction 50 is lowered (that is, Δh11 is lengthened), the endpoint 14a of the edge 14 goes farther away from the endpoint 103a of the edge 103 of the blocking member 102 in the comparative example, causing the vertex v11 of the penumbra region PR11 to go farther away from the vertex v10. Thus, by lowering the position p11 of the edge 14 in the direction 50 (that is, lengthening Δh11), the side S11 of the penumbra region PR11 may be lengthened.

Next, the edge 15 of the blocking member 12 will be described.

As shown in FIG. 24, the edge 15 is a straight edge (with length q15) extending from the other endpoint 13b of the arcuate edge 13 in the direction 40 perpendicular to the plane S1. The edge 15 has one endpoint 15a connected to the endpoint 13b of the arcuate edge 13 and the other endpoint 15b lying opposite to the one endpoint 15a. The edge 15 is formed to have positions of the endpoints 15a and 15b in the direction 50 at the same position p12. While the length q15 of the edge 15 is equal to the length q14 of the edge 14 (q14=q15) in the first embodiment, it is possible to set so that q14≠q15.

In FIG. 24 is also shown a line L12 projected on the XY-plane. The line L12 overlies the focal spot f and the other endpoint 103b of the edge 103 of the blocking member 102 in the comparative example in the XY-plane. In the first embodiment, the endpoint 15b of the edge 15 lies at a position on the line L12 projected on the XY-plane, the position being away from the other endpoint 103b of the edge 103 of the blocking member 102 in the comparative example by Δg12 toward the X-ray detector 75.

The edge 15 is formed at the position p12 lower than a position p120 of the endpoint 103b of the edge 103 of the blocking member 102 in the comparative example in the direction 50 by Δh12. Therefore, the edge 15 is formed to lie on the side of the X-ray detector 75 relative to the arc A12 contiguous to the arc A1. In FIG. 24, a region re12 surrounded by the arc A12, line L12, and edge 15 is hatched. Since the edge 103 of the blocking member 102 in the comparative example extends on the arc A12, when the blocking member 102 in the comparative example is used, an X-ray beam traveling toward the region re12 reaches the X-ray detector 75 without being blocked by the blocking member 102 in the comparative example. However, since in the blocking member 12 in the first embodiment, the edge 15 is formed on the side of the X-ray detector 75 relative to the arc A12, when the blocking member 12 in the first embodiment is used, an X-ray beam traveling toward the region re12 may be blocked by the portion of the edge 15 of the blocking member 12. Therefore, a penumbra region PR12 may be formed in a corner 752 of the detector 75 (see FIGS. 21 and 22). The endpoint 15a of the edge 15 corresponds to a vertex v12 of the penumbra region PR12 (see FIG. 22). Therefore, a side S12 of the penumbra region PR12 in the direction 40 (x direction) may be adjusted to a desired length by adjusting the position p12 of the edge 15 in the direction 50 (see FIG. 24). For example, as the position p12 of the edge 15 in the direction 50 is heightened (that is, Δh12 is shortened), the endpoint 15a of the edge 15 comes closer to the endpoint 103b of the edge 103 of the blocking member 102 in the comparative example, causing the vertex v12 of the penumbra region PR12 to come closer to a vertex v120. Thus, as the position p12 of the edge 15 in the direction 50 is heightened (that is, Δh12 is shortened), the side S12 of the penumbra region PR12 may be shortened. On the other hand, as the position p12 of the edge 15 in the direction 50 is lowered (that is, Δh12 is lengthened), the endpoint 15a of the edge 15 goes farther away from the endpoint 103b of the edge 103 of the blocking member 102 in the comparative example, causing the vertex v12 of the penumbra region PR12 to go farther away from the vertex v120. Thus, by lowering the position p12 of the edge 15 in the direction 50 (that is, lengthening Δh12), the side S12 of the penumbra region PR12 may be lengthened.

Next, the other blocking member 22 will be described.

Figure 25:
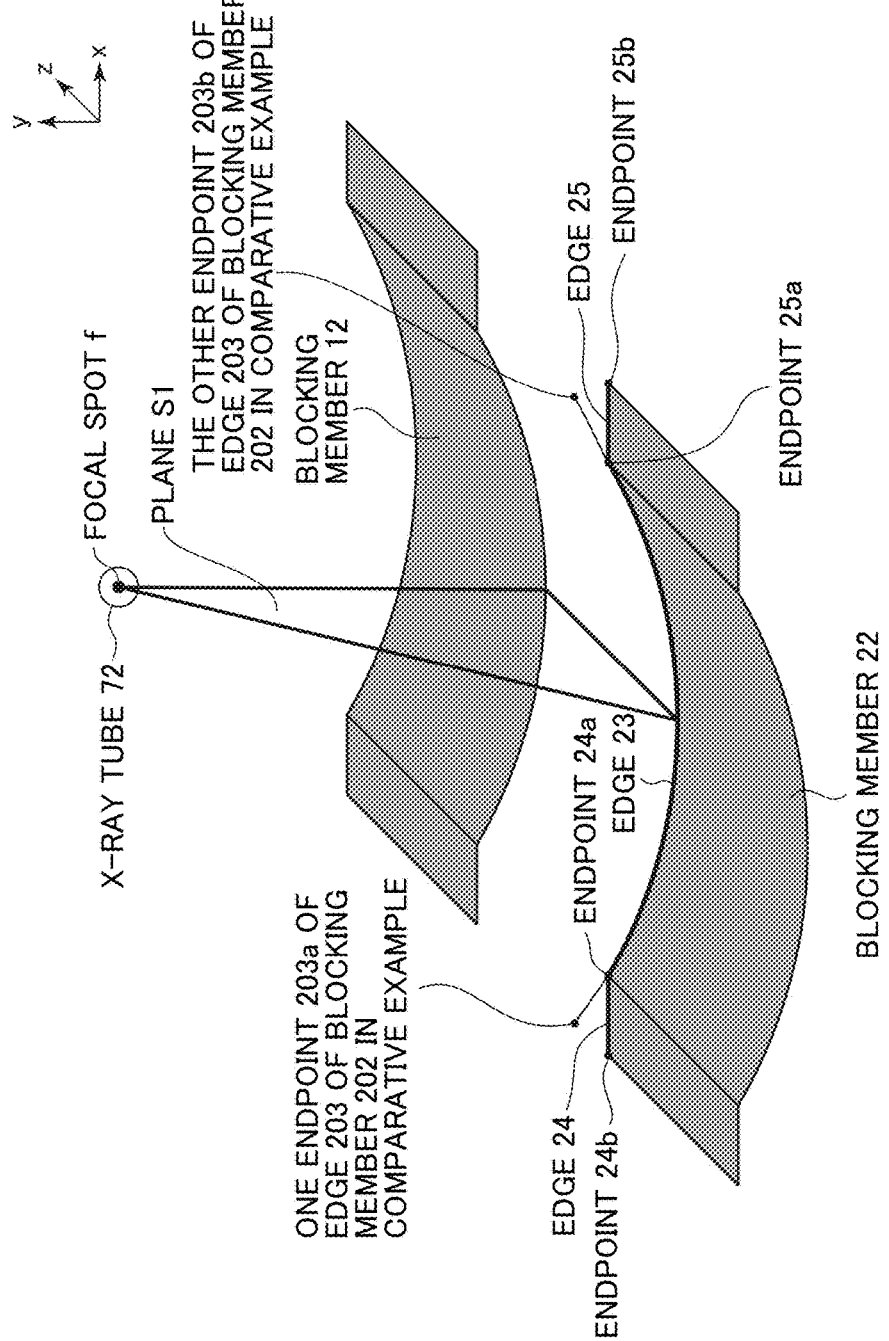
FIG. 25 is an enlarged perspective view of a blocking member 22 in FIG. 21.
Figure 26:
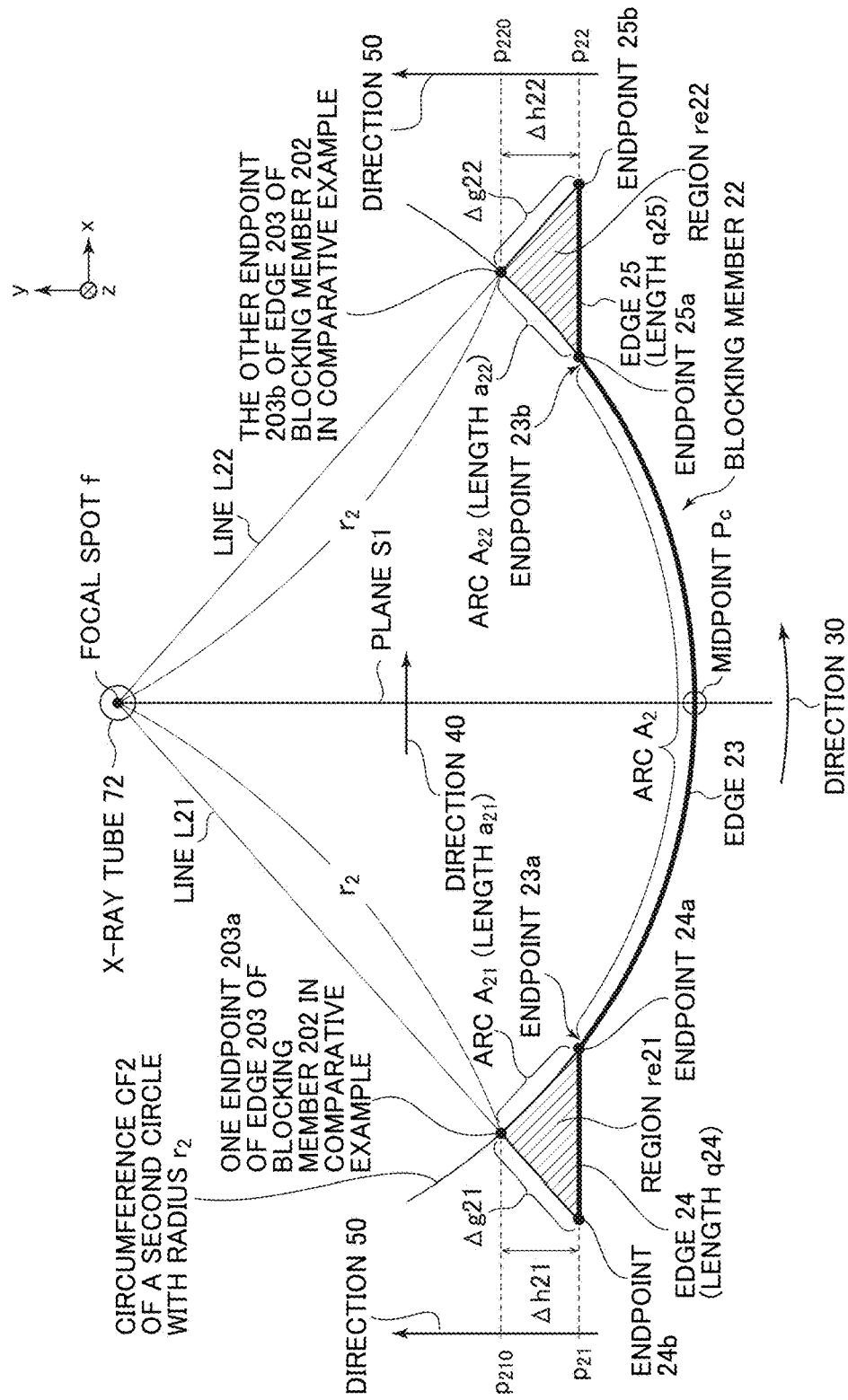
FIG. 26 is a diagram showing the shape of edges of the blocking member 22 in the XY-plane.

FIGS. 25 and 26 are explanatory diagrams for edges of the blocking member 22.

FIG. 25 is an enlarged perspective view of the blocking member 22, and FIG. 26 is a diagram showing the shape of the edges of the blocking member 22 in the XY-plane.

The blocking member 22 has an edge 23, an edge 24, and an edge 25.

As shown in FIG. 26, the edge 23 of the blocking member 22 is formed on an arc A2 lying on the circumference CF2 of the second circle with radius r2 around the focal spot f in the XY-plane. Therefore, the edge 23 of the blocking member 22 lies on the circumference CF2 of the second circle with radius r2, which is similar to the edge 203 of the blocking member 202 in the comparative example (see FIG. 15) in this regard. The edge 23 of the blocking member 22 in the first embodiment, however, is formed to be shorter than the edge 203 of the blocking member 202 in the comparative example. In FIGS. 25 and 26, the one endpoint 203a and the other endpoint 203b of the edge 203 of the blocking member 202 in the comparative example are shown to clarify the difference between the length of the edge 23 of the blocking member 22 in the first embodiment and that of the edge 203 of the blocking member 202 in the comparative example. The edge 23 of the blocking member 22 in the first embodiment is formed to be shorter than the edge 203 of the blocking member 202 in the comparative example by the total length (a21+a22) of a length a21 of an arc A21 and a length a22 of an arc A22, the arcs A21 and A22 lying on the circumference CF2 of the second circle with radius r2. While a21 and a22 are set so that a21=a22 in the first embodiment, it is possible to set them so that a21≠a22. Moreover, in the first embodiment, all and a12 (see FIGS. 23 and 24) and a21 and a22 (see FIGS. 25 and 26) are set to satisfy the equation below:

$$a11=a12=a21=a22 \tag{1}$$

However, it is possible to set at least one of the lengths a11, a12, a21, and a22 to be different from the remaining lengths.

Moreover, the blocking member 22 in the first embodiment is formed to have two straight edges 24 and 25, in addition to the arcuate edge 23.

In FIG. 26 is shown the plane S1. The plane S1 shown in FIG. 26 is identical to the plane S1 shown in FIG. 24, which contains a midpoint PC of the edge 23 in the direction 30 along the circumference CF2, and the focal spot f, and also is parallel to the body-axis direction (z-direction). The edges 24 and 25 lie opposite to each other with respect to the plane S1.

Now the edges 24 and 25 will be described one by one.

The edge 24 is a straight edge (with length q24) extending from one endpoint 23a of the arcuate edge 23 in a direction opposite to the direction 40 perpendicular to the plane S1. The edge 24 has one endpoint 24a connected to the endpoint 23a of the arcuate edge 23 and the other endpoint 24b lying opposite to the one endpoint 24a. The edge 24 is formed to have positions of the endpoints 24a and 24b in the direction 50 at the same position p21.

In FIG. 26 is also shown a line L21 projected on the XY-plane. The line L21 overlies the focal spot f and the one endpoint 203a of the edge 203 of the blocking member 202 in the comparative example in the XY-plane. In the first embodiment, the endpoint 24b of the edge 24 lies at a position on the line L21 projected on the XY-plane, the position being away from the one endpoint 203a of the edge 203 of the blocking member 202 in the comparative example by Δg21 toward the X-ray detector 75.

The edge 24 is formed at the position p21 lower than a position p210 of the endpoint 203a of the edge 203 of the blocking member 202 in the comparative example in the direction 50 by Δh21 Therefore, the edge 24 is formed to lie on the side of the X-ray detector 75 relative to the arc A21 contiguous to the arc A2. In FIG. 26, a region re21 surrounded by the arc A21, line L11, and edge 24 is hatched. Since the edge 203 of the blocking member 202 in the comparative example extends on the arc A21, when the blocking member 202 in the comparative example is used, an X-ray beam traveling toward the region re21 reaches the X-ray detector 75 without being blocked by the blocking member 202 in the comparative example. However, since in the blocking member 22 in the first embodiment, the edge 24 is formed on the side of the X-ray detector 75 relative to the arc A21, when the blocking member 22 in the first embodiment is used, the X-ray beam traveling toward the region re21 may be blocked by the portion of the edge 24 of the blocking member 22. Therefore, a penumbra region PR21 may be formed in a corner 753 of the detector 75 (see FIGS. 21 and 22). The endpoint 24a of the edge 24 corresponds to a vertex v21 of the penumbra region PR21. Therefore, a side S21 of the penumbra region PR21 in the direction 40 (x direction) may be adjusted to a desired length by adjusting the position p11 of the edge 24 in the direction 50 (see FIG. 26). For example, as the position p21 of the edge 24 in the direction 50 is heightened (that is, Δh21 is shortened), the endpoint 24a of the edge 24 comes closer to the endpoint 203a of the edge 203 of the blocking member 202 in the comparative example, causing the vertex v21 of the penumbra region PR21 to come closer to a vertex v210. Thus, as the position p21 of the edge 24 in the direction 50 is heightened (that is, Δh21 is shortened), the side S21 of the penumbra region PR21 may be shortened. On the other hand, as the position p21 of the edge 24 in the direction 50 is lowered (that is, Δh21 is lengthened), the endpoint 24a of the edge 24 goes farther away from the endpoint 203a of the edge 203 of the blocking member 202 in the comparative example, causing the vertex v21 of the penumbra region PR21 to go farther away from the vertex v210. Thus, by lowering the position p21 of the edge 24 in the direction 50 (that is, lengthening Δh21), the side S21 of the penumbra region PR21 may be lengthened.

The blocking member 22 further has the edge 25.

The edge 25 is a straight edge (with length q25) extending from the other endpoint 23b of the arcuate edge 23 in the direction 40 perpendicular to the plane S1. The edge 25 has one endpoint 25a connected to the endpoint 23b of the arcuate edge 23 and the other endpoint 25b lying opposite to the one endpoint 25a. The edge 25 is formed to have positions of the endpoints 25a and 25b in the direction 50 at the same position p22. While the length q25 of the edge 25 is equal to the length q24 of the edge 24 (q24=q25) in the first embodiment, it is possible to set so that q24≠q25. In the first embodiment, the lengths q14 and q15 of the edges 14 and 15 (see FIG. 24) and the lengths q24 and q25 of the edges 24 and 25 (see FIG. 26) are set to satisfy the equation below:

$$Q14=q15=q24=q25 \tag{2}$$

However, it is possible to set at least one of the lengths q14, q15, q24, q25 to be different from the remaining lengths.

In FIG. 26 is also shown a line L22 projected on the XY-plane. The line L22 overlies the focal spot f and the other endpoint 203b of the edge 203 of the blocking member 202 in the comparative example in the XY-plane. In the first embodiment, the endpoint 25b of the edge 25 lies at a position on the line L22 projected on the XY-plane, the position being away from the other endpoint 203b of the edge 203 of the blocking member 202 in the comparative example by Δg22 toward the X-ray detector 75.

The edge 25 is formed at the position p22 lower than a position p220 of the endpoint 203b of the edge 203 of the blocking member 202 in the comparative example in the direction 50 by Δh22. Therefore, the edge 25 is formed to lie on the side of the X-ray detector 75 relative to the arc A22 contiguous to the arc A2. In FIG. 26, a region re22 surrounded by the arc A22, line L22, and edge 25 is hatched. Since the edge 203 of the blocking member 202 in the comparative example extends on the arc A22, when the blocking member 202 in the comparative example is used, an X-ray beam traveling toward the region re22 reaches the X-ray detector 75 without being blocked by the blocking member 202 in the comparative example. However, since in the blocking member 22 in the first embodiment, the edge 25 is formed on the side of the X-ray detector 75 relative to the arc A22, when the blocking member 22 in the first embodiment is used, the X-ray beam traveling toward the region re22 may be blocked by the portion of the edge 25 of the blocking member 22. Therefore, a penumbra region PR22 may be formed in a corner 754 of the detector 75 (see FIGS.

21 and 22). The endpoint 25a of the edge 25 corresponds to a vertex v22 of the penumbra region PR22 (see FIG. 22). Therefore, a side S22 of the penumbra region PR22 in the direction 40 (x direction) may be adjusted to a desired length by adjusting the position p22 of the edge 25 in the direction 50 (see FIG. 26). For example, as the position p22 of the edge 25 in the direction 50 is heightened (that is, Δh22 is shortened), the endpoint 25a of the edge 25 comes closer to the endpoint 203b of the edge 203 of the blocking member 202 in the comparative example, causing the vertex v22 of the penumbra region PR22 to come closer to a vertex v220. Thus, as the position p22 of the edge 25 in the direction 50 is heightened (that is, Δh22 is shortened), the side S22 of the penumbra region PR22 may be shortened. On the other hand, as the position p22 of the edge 25 in the direction 50 is lowered (that is, Δh22 is lengthened), the endpoint 25a of the edge 25 goes farther away from the endpoint 203b of the edge 203 of the blocking member 202 in the comparative example, causing the vertex v22 of the penumbra region PR22 to go farther away from the vertex v220. Thus, by lowering the position p22 of the edge 25 in the direction 50 (that is, lengthening Δh22), the side S22 of the penumbra region PR22 may be lengthened.

As described above referring to FIGS. 21 to 26, the blocking members 12 and 22 in the first embodiment have the edges 14, 15, 24, and 25 on the side of the X-ray detector 75 relative to the arcs A11, A12, A21, and A22, and thus, X-ray beams traveling toward the regions re11, re12, re21, and re22 may be blocked. Therefore, as shown in FIGS. 21 and 22, the X-ray detector 75 may be provided in its four corners with the penumbra regions PR11, PR12, PR21, and PR22 corresponding to the regions re11, re12, re21, and re22. Thus, the projected region (umbra region) R10 obtained by the blocking members 12 and 22 in the first embodiment may be shaped to contain none of the four corners of the X-ray detector 75.

In the case that the blocking members 102 and 202 in the comparative example are used as described earlier and the aperture width W is set to W=Wm as shown in FIG. 16, no penumbra region can be created in the X-ray detector 75, so that there is a problem that beam tracking cannot be applied. In contrast, in the first embodiment, X-ray beams traveling toward the regions re11, re12, re21, and re22 may be blocked by the edges 14 and 15 of the blocking member 12 and the edges 24 and 25 of the blocking member 22. Therefore, when the blocking members 12 and 22 in the first embodiment are used, the X-ray detector 75 may be provided in its four corners with the penumbra regions PR11, PR12, PR21, and PR22 (see FIGS. 21 and 22), so that beam tracking may be still applied when the aperture width W is set to W=Wm.

As shown in FIG. 22, the edges 13, 14, and 15 of the blocking member 12 collinearly extend in the direction 40 in a plane (corresponding to ZX-plane in FIG. 22) perpendicular to the XY-plane and the plane S1. Likewise, the edges 23, 24, and 25 of the blocking member 22 collinearly extend in the direction 40 in the plane (corresponding to ZX-plane in FIG. 22) perpendicular to the XY-plane and the plane S1. Thus, in the first embodiment, it is unnecessary to provide the blocking members 12 and 22 with the protrusions e1 to e4 (see FIG. 18) for forming penumbra regions, and therefore, penumbra regions may be created without a limitation on the aperture width W1 (see FIG. 18) otherwise imposed when the protrusions e1 to e4 are provided.

In the first embodiment, the lengths of the edges 14 and 15 of the blocking member 12 are set to q14 and q15, respectively (see FIG. 24). However, edges longer than the edges 14 and 15 may be formed in place of the edges 14 and 15 (see FIG. 27).

Figure 27:
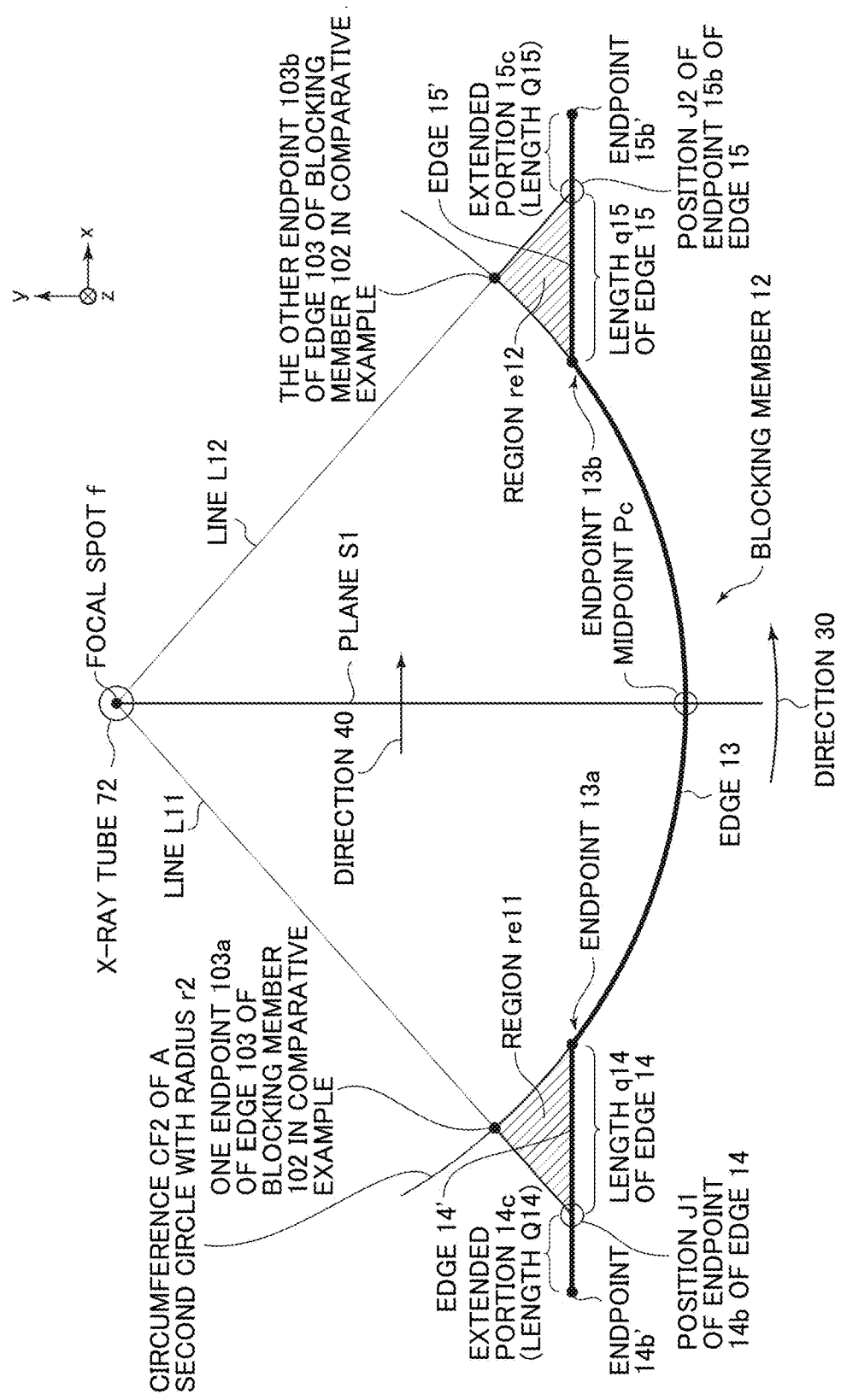
FIG. 27 is a diagram showing an example in which edges longer than edges 14 and 15 are formed in place of the edges 14 and 15.

FIG. 27 is a diagram showing a case in which edges longer than the edges 14 and 15 are formed in place of the edges 14 and 15. In FIG. 27, an edge 14' designates an edge formed longer than the edge 14 by an extended portion 14c, and an edge 15' designates an edge formed longer than the edge 15 by an extended portion 15c.

An endpoint 14b' of the edge 14' is disposed at a position offset from a position J1 of the endpoint 14b of the edge 14 by the length Q14 of the extended portion 14c in a direction opposite to the direction 40. An endpoint 15b' of the edge 15' is disposed at a position offset from a position J2 of the endpoint 15b of the edge 15 by a length Q15 of the extended portion 15c in the direction 40. When the edges 14' and 15' are formed in place of the edges 14 and 15, again, X-rays traveling toward the regions re11 and re12 are blocked. Therefore, beam tracking may be still applied when the edges 14' and 15' are formed in place of the edges 14 and 15. The edge 14' may have the same length as or a length different from the edge 15'. In FIG. 27, the extended portion 14c of the edge 14' and the extended portion 15c of the edge 15' are parallel to the direction 40. However, these extended portions may be formed obliquely to the direction 40.

While the blocking member 12 is described with reference to FIG. 27, the edges 24 and 25 of the blocking member 22 may be longer insofar as penumbra regions can be secured. Moreover, it is possible to make the edge(s) of one of the blocking members 12 and 22 longer than the edge(s) of the other.

Next, the difference between the beam shape on the X-ray detector when the blocking members 12 and 22 in the first embodiment are used and that when the blocking members 102 and 202 in the comparative example are used will be described referring to FIG. 28.

The upper part of FIG. 28 is a graph representing the beam shape on an X-ray detector when the blocking members 102 and 202 in the comparative example are used, and the lower part of FIG. 28 is a graph representing the beam shape on the X-ray detector when the blocking members 12 and 22 in the first embodiment are used.

The horizontal axis in the graphs represents the position of the detector elements in a channel direction, and the vertical axis represents the position of the detector elements in a row direction.

In the graphs are shown the beam shape for coverage of 80 mm and that for coverage of 40 mm.

When the blocking members 102 and 202 in the comparative example are used, the beam width is unchanged regardless of the position in the X-ray detector in the channel direction, so that a penumbra region for applying beam tracking cannot be obtained in four corners of the X-ray detector.

On the other hand, when the blocking members 12 and 22 in the first embodiment are used, it can be seen that penumbra regions for applying beam tracking may be obtained in the four corners of the X-ray detector because the beam width may be reduced at both ends of the X-ray detector in the channel direction.

(2) Second Embodiment

As compared with the first embodiment, a second embodiment is different in edges of the blocking members of the aperture. Now the second embodiment will be described.

FIGS. 29 to 34 are explanatory diagrams for edges of blocking members 32 and 42 in the second embodiment. Now the drawings will be described.

Figure 29:
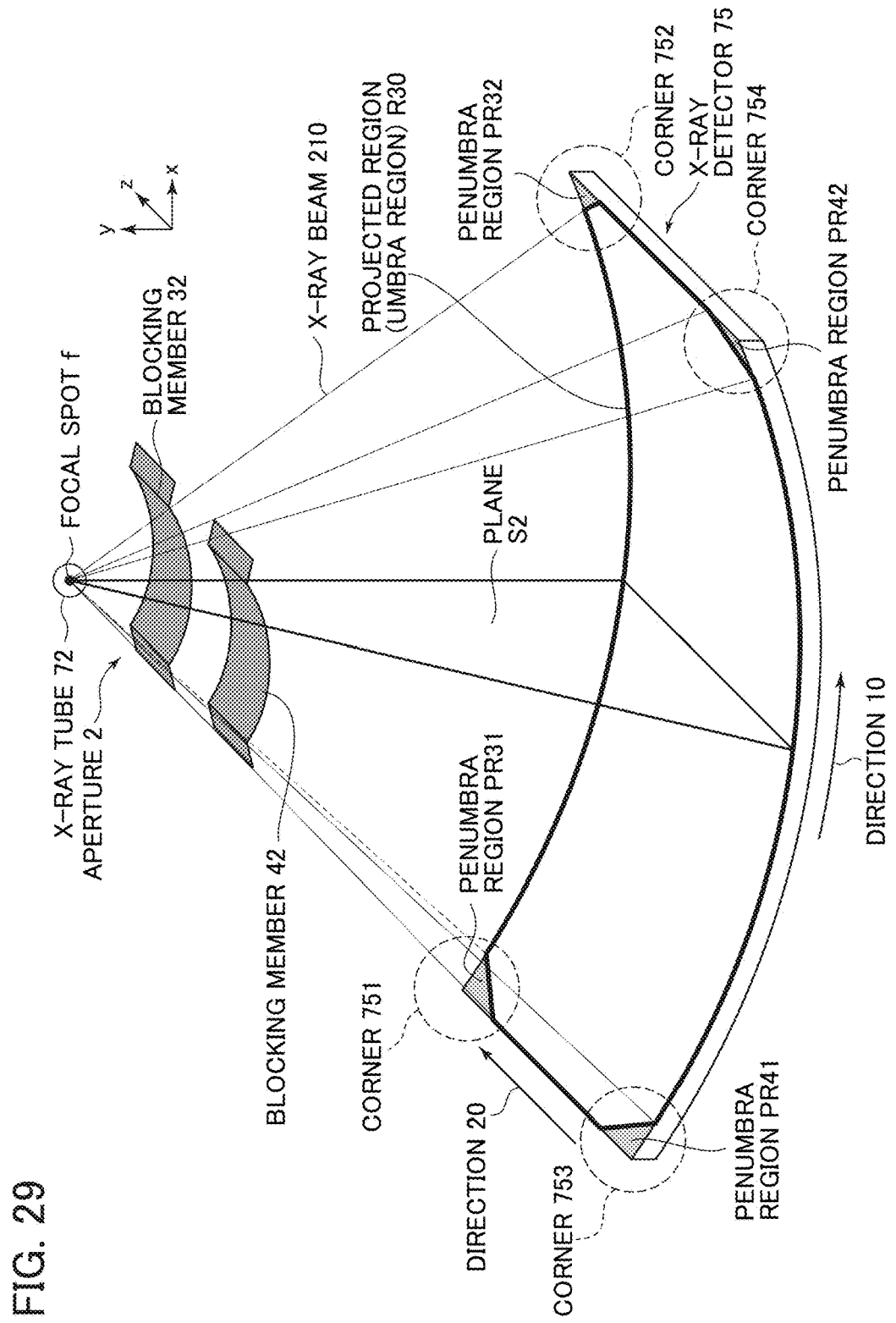
FIG. 29 is a perspective view of an aperture 2 in a second embodiment and the X-ray detector 75.
Figure 30:
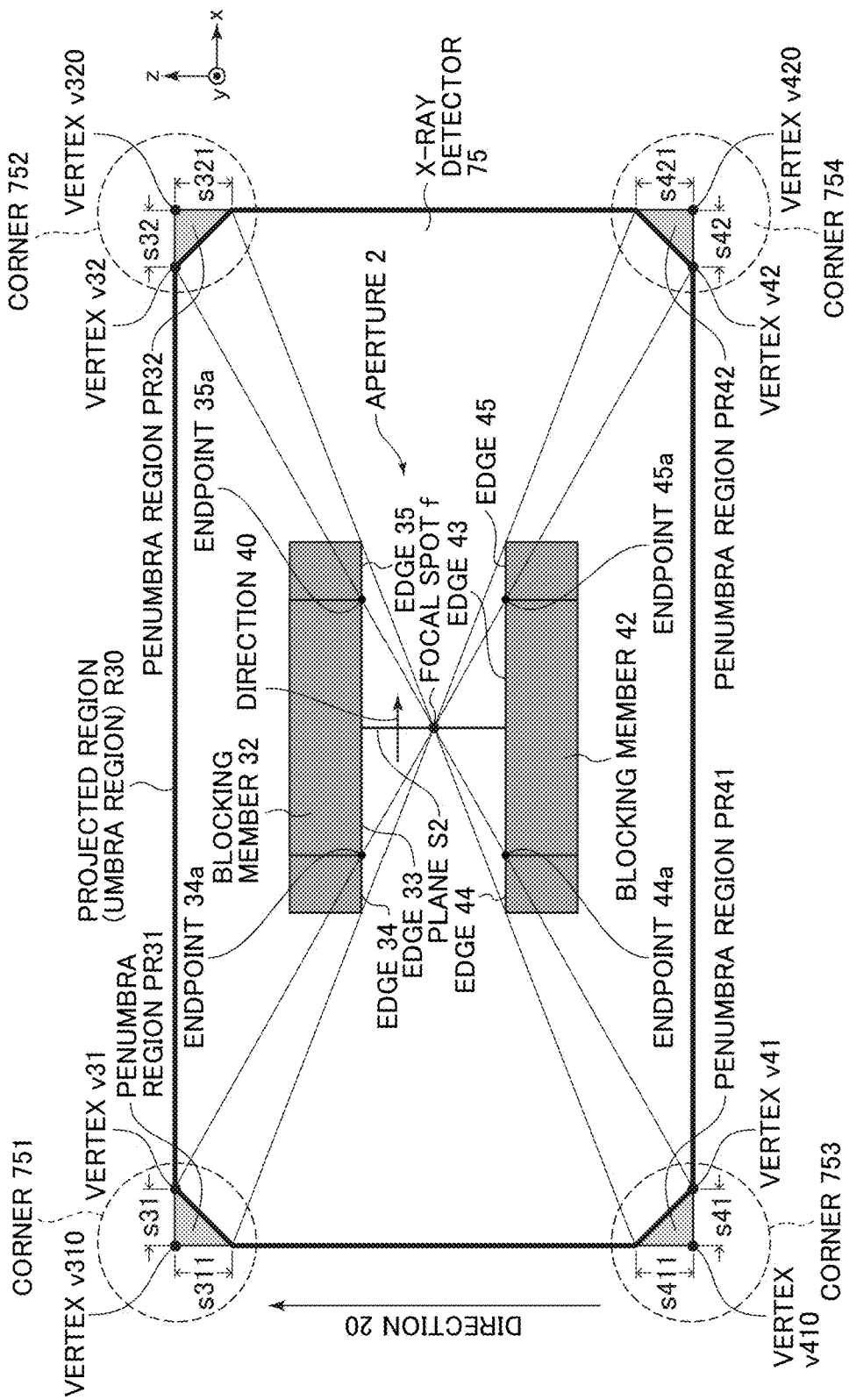
FIG. 30 is a plan view of the aperture 2 and X-ray detector 75 as viewed from a focal spot f.

FIG. 29 is a perspective view of an aperture 2 and the X-ray detector 75 in the second embodiment, and FIG. 30 is a plan view of the aperture 2 and X-ray detector 75 as viewed from the focal spot f. In FIGS. 29 and 30, for the aperture 2, only the blocking members 32 and 42 are shown and supporting members for supporting them are not shown for convenience of explanation, as in the first embodiment.

The blocking members 32 and 42 in the aperture 2 are disposed opposite to each other in the body-axis direction (z-direction). It is by the blocking members 32 and 42 that the z-extent of the X-ray beam 210 is defined.

Now edges of the blocking members 32 and 42 in the aperture 2 will be described one by one.

Figure 31:
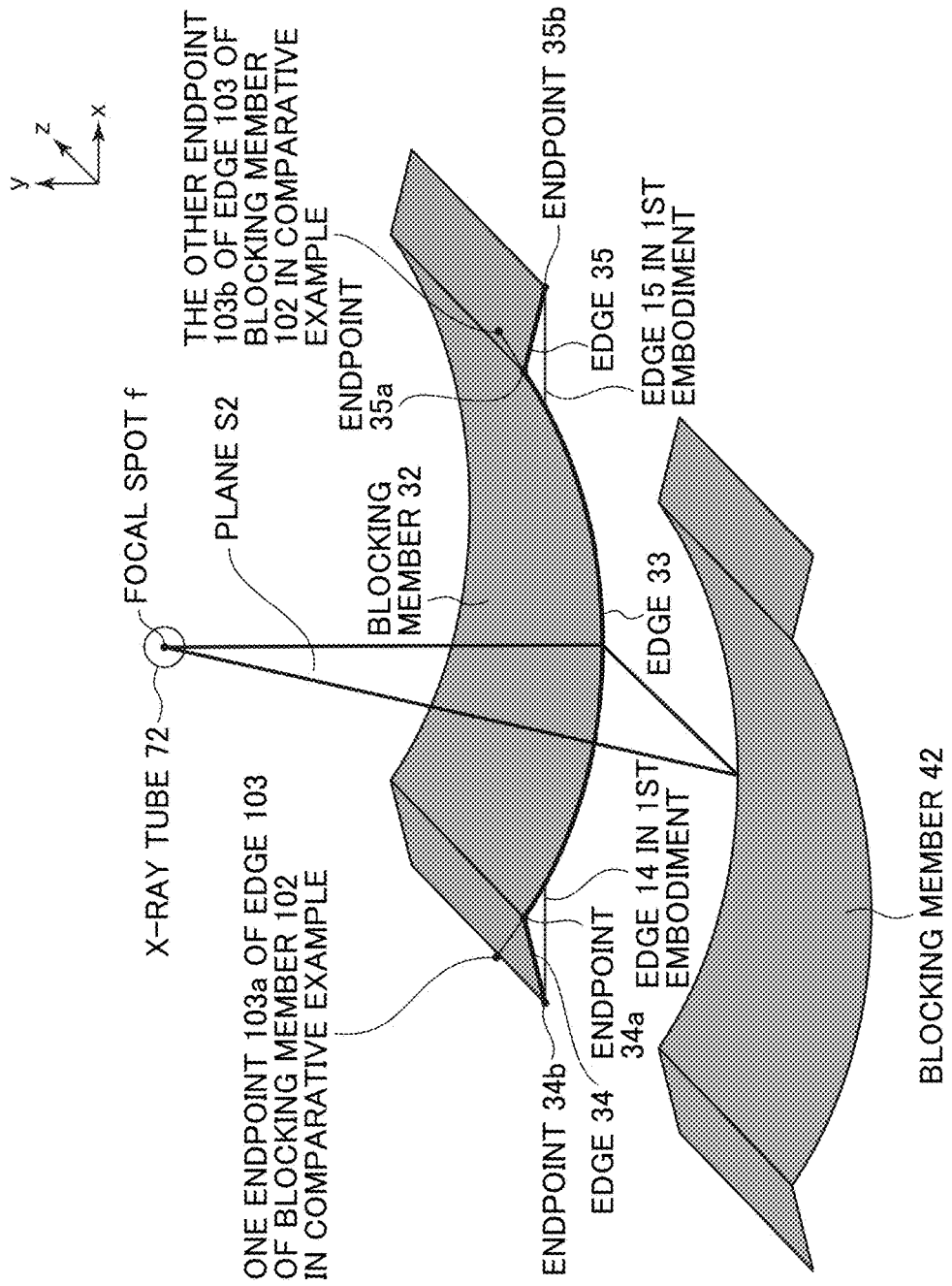
FIG. 31 is an enlarged perspective view of a blocking member 32 in FIG. 29.
Figure 32:
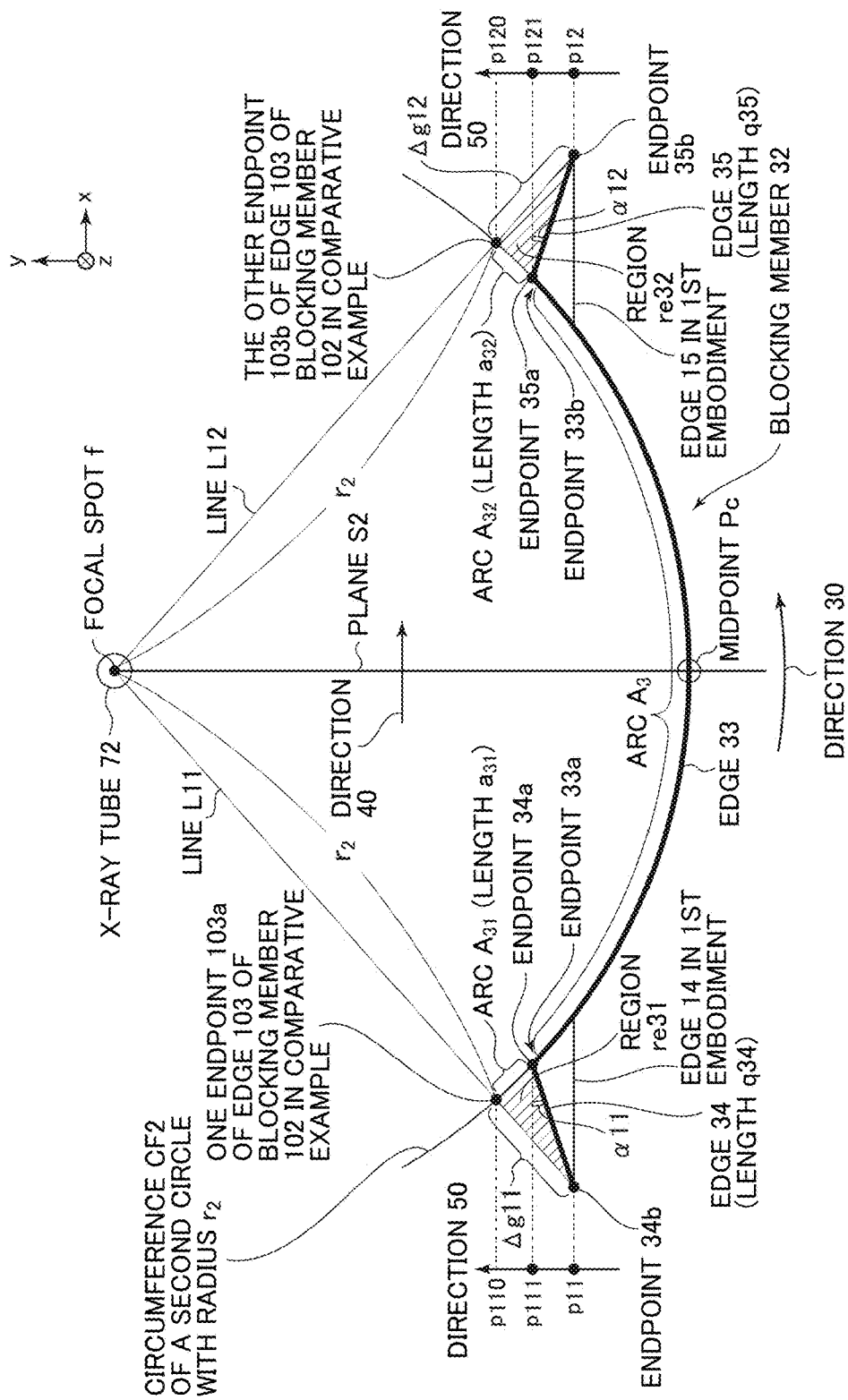
FIG. 32 is a diagram showing the shape of edges of the blocking member 32 in the XY-plane.

FIGS. 31 and 32 are explanatory diagrams for edges of the blocking member 32.

FIG. 31 is an enlarged perspective view of the blocking member 32, and FIG. 32 is a diagram showing the shape of the edges of the blocking member 32 in the XY-plane.

The blocking member 32 has an edge 33, an edge 34, and an edge 35.

As shown in FIG. 32, the edge 33 of the blocking member 32 is formed on an arc A3 lying on the circumference CF2 of the second circle with radius r2 around the focal spot f in the XY-plane. Therefore, the edge 33 of the blocking member 32 lies on the circumference CF2 of the second circle with radius r2, which is similar to the edge 103 of the blocking member 102 in the comparative example (see FIG. 14) in this regard. The edge 33 of the blocking member 32 in the second embodiment, however, is formed to be shorter than the edge 103 of the blocking member 102 in the comparative example. In FIGS. 31 and 32, the one endpoint 103a and the other endpoint 103b of the edge 103 of the blocking member 102 in the comparative example are shown to clarify the difference between the length of the edge 33 of the blocking member 32 in the second embodiment and that of the edge 103 of the blocking member 102 in the comparative example. The edge 33 of the blocking member 32 in the second embodiment is formed to be shorter than the edge 103 of the blocking member 102 in the comparative example by the total length (a31+a32) of a length a31 of an arc A31 and a length a32 of an arc A32, the arcs A31 and A32 lying on the circumference CF2 of the second circle with radius r2. While a31 and a32 are set so that a31=a32 in the second embodiment, it is possible to set them so that a31≠a32.

Moreover, the blocking member 32 in the second embodiment is formed to have two straight edges 34 and 35, in addition to the arcuate edge 33.

In FIG. 32 is shown a plane S2. The plane S2 contains a midpoint PC of the edge 33 in the direction 30 along the circumference CF2, and the focal spot f, and also is parallel to the body-axis direction (z-direction). The edges 34 and 35 lie opposite to each other with respect to the plane S2.

Now the edges 34 and 35 will be described one by one.

The edge 34 is a straight edge (with length q34) extending from one end point 33a of the arcuate edge 33 obliquely to the direction 40 perpendicular to the plane S2, and is oblique to the direction 40 by an angle α11. The edge 34 has one endpoint 34a connected to the endpoint 33a of the arcuate edge 33 and the other endpoint 34b lying opposite to the one endpoint 34a. When the direction 50 (corresponding to the y-direction in FIG. 32) parallel to the plane S2 and perpendicular to the direction 40 is considered, the edge 34 is formed to have a position p111 of the endpoint 34a in the direction 50 higher than the position p11 of the endpoint 34b in the direction 50.

In FIG. 32 is also shown the line L11 projected on the XY-plane. The line L11 overlies the focal spot f and the one endpoint 103a of the edge 103 of the blocking member 102 in the comparative example in the XY-plane. In the second embodiment, the endpoint 34b of the edge 34 lies at a position on the line L11 projected on the XY-plane, the position being away from the one endpoint 103a of the edge 103 of the blocking member 102 in the comparative example by Δg11 toward the X-ray detector 75. Therefore, the edge 34 is formed to lie on the side of the X-ray detector 75 relative to the arc A31 contiguous to the arc A3. In FIG. 32, a region re31 surrounded by the arc A31, line L11, and edge 34 is hatched. Since the edge 103 of the blocking member 102 in the comparative example extends on the arc A31, when the blocking member 102 in the comparative example is used, an X-ray beam traveling toward the region re31 reaches the X-ray detector 75 without being blocked by the blocking member 102 in the comparative example. However, since in the blocking member 32 in the second embodiment, the edge 34 is formed on the side of the X-ray detector 75 relative to the arc A31, when the blocking member 32 in the second embodiment is used, the X-ray beam traveling toward the region re31 may be blocked by the portion of the edge 34 of the blocking member 32. Therefore, a penumbra region PR31 may be formed in the corner 751 of the detector 75 (see FIGS. 29 and 30). The endpoint 34a of the edge 34 corresponds to a vertex v31 of the penumbra region PR31. Therefore, a side S31 of the penumbra region PR31 in the direction 40 (x direction) may be adjusted to a desired length by adjusting the position p111 of the endpoint 34a of the edge 34 in the direction 50 (see FIG. 32). For example, as the position p111 of the endpoint 34a of the edge 34 in the direction 50 is heightened, the endpoint 34a of the edge 34 comes closer to the endpoint 103a of the edge 103 of the blocking member 102 in the comparative example, causing the vertex v31 of the penumbra region PR31 to come closer to a vertex v310. Thus, by heightening the position p111 of the endpoint 34a of the edge 34 in the direction 50, the side S31 of the penumbra region PR31 may be shortened. On the other hand, as the position p111 of the endpoint 34a of the edge 34 in the direction 50 is lowered, the endpoint 34a of the edge 34 goes farther away from the endpoint 103a of the edge 103 of the blocking member 102 in the comparative example, causing the vertex v31 of the penumbra region PR31 to go farther away from the vertex v310. Thus, by lowering the position p111 of the endpoint 34a of the edge 34 in the direction 50, the side S31 of the penumbra region PR31 may be lengthened.

Moreover, a side S311 of the penumbra region PR31 in the direction 20 (z direction) may be shortened by narrowing the angle α11 while fixing the position of the endpoint 34a of the edge 34; on the other hand, the side S311 of the penumbra region PR31 may be lengthened by widening the angle α11 while fixing the position of the endpoint 34a of the edge 34.

In FIGS. 31 and 32, the edge 14 in the first embodiment is also shown as a reference to clarify the difference between the edge 34 in the second embodiment and the edge 14 in the first embodiment. The edge 34 in the second embodiment is formed to be oblique as compared with the edge 14 in the first embodiment by the angle α=α11.

Next, the edge 35 of the blocking member 32 will be described.

The edge 35 is a straight edge (with length q35) extending from the other endpoint 33b of the arcuate edge 33 obliquely to the direction 40 perpendicular to the plane S2, and is oblique to the direction 40 by an angle α12. The edge 35 has one endpoint 35a connected to the endpoint 33b of the arcuate edge 33, and the other endpoint 35b lying opposite to the one point 35a. The edge 35 is formed to have a position p121 of the endpoint 35a in the direction 50 higher than the position p12 of the endpoint 35b in the direction 50. While the length q35 of the edge 35 is equal to the length q34 of the edge 34 (q34=q35) in the second embodiment, it is possible to set so that q34≠q35.

In FIG. 32 is also shown the line L12 projected on the XY-plane. The line L12 overlies the focal spot f and the other endpoint 103b of the edge 103 of the blocking member 102 in the comparative example in the XY-plane. In the second embodiment, the endpoint 35b of the edge 35 lies at a position on the line L12 projected on the XY-plane, the position being away from the other endpoint 103b of the edge 103 of the blocking member 102 in the comparative example by Δg12 toward the X-ray detector 75. Therefore, the edge 35 is formed to lie on the side of the X-ray detector 75 relative to the arc A32 contiguous to the arc A3. In FIG. 32, a region re32 surrounded by the arc A32, line L12, and edge 35 is hatched. Since the edge 103 of the blocking member 102 in the comparative example extends on the arc A32, when the blocking member 102 in the comparative example is used, an X-ray beam traveling toward the region re32 reaches the X-ray detector 75 without being blocked by the blocking member 102 in the comparative example. However, since in the blocking member 32 in the second embodiment, the edge 35 is formed on the side of the X-ray detector 75 relative to the arc A32, when the blocking member 32 in the second embodiment is used, the X-ray beam traveling toward the region re32 may be blocked by the portion of the edge 35 of the blocking member 32. Therefore, a penumbra region PR32 may be formed in the corner 752 of the detector 75 (see FIGS. 29 and 30). The endpoint 35a of the edge 35 corresponds to a vertex v32 of the penumbra region PR32. Therefore, a side S32 of the penumbra region PR32 in the direction 40 (x direction) may be adjusted to a desired length by adjusting the position p121 of the endpoint 35a of the edge 35 in the direction 50 (see FIG. 32). For example, as the position p121 of the edge 35 in the direction 50 is heightened, the endpoint 35a of the edge 35 comes closer to the endpoint 103b of the edge 103 of the blocking member 102 in the comparative example, causing the vertex v32 of the penumbra region PR32 to come closer to a vertex v320. Thus, by heightening the position p121 of the endpoint 35a of the edge 35 in the direction 50, the side S32 of the penumbra region PR32 may be shortened. On the other hand, as the position p121 of the endpoint 35a of the edge 35 in the direction 50 is lowered, the endpoint 35a of the edge 35 goes farther away from the endpoint 103b of the edge 103 of the blocking member 102 in the comparative example, causing the vertex v32 of the penumbra region PR32 to go farther away from the vertex v320. Thus, by lowering the position p121 of the endpoint 35a of the edge 35 in the direction 50, the side S32 of the penumbra region PR32 may be lengthened.

Moreover, a side S321 of the penumbra region PR32 in the direction 20 (z direction) may be shortened by narrowing the angle α21 while fixing the position of the endpoint 35a of the edge 35; on the other hand, the side S321 of the penumbra region PR32 may be lengthened by widening the angle α21 while fixing the position of the endpoint 35a of the edge 35.

In FIGS. 31 and 32, the edge 15 in the first embodiment is also shown as a reference to clarify the difference between the edge 35 in the second embodiment and the edge 15 in the first embodiment. The edge 35 in the second embodiment is formed to be oblique as compared with the edge 15 in the first embodiment by the angle α=α12. Moreover, while the angle α11 of the edge 34 and the angle α12 of the edge 35 are set so that $\alpha_{11}=\alpha_{12}$ in the second embodiment, it is possible to set them so that $\alpha_{11} \neq \alpha_{12}$.

Next, the other blocking member 42 will be described.

Figure 33:
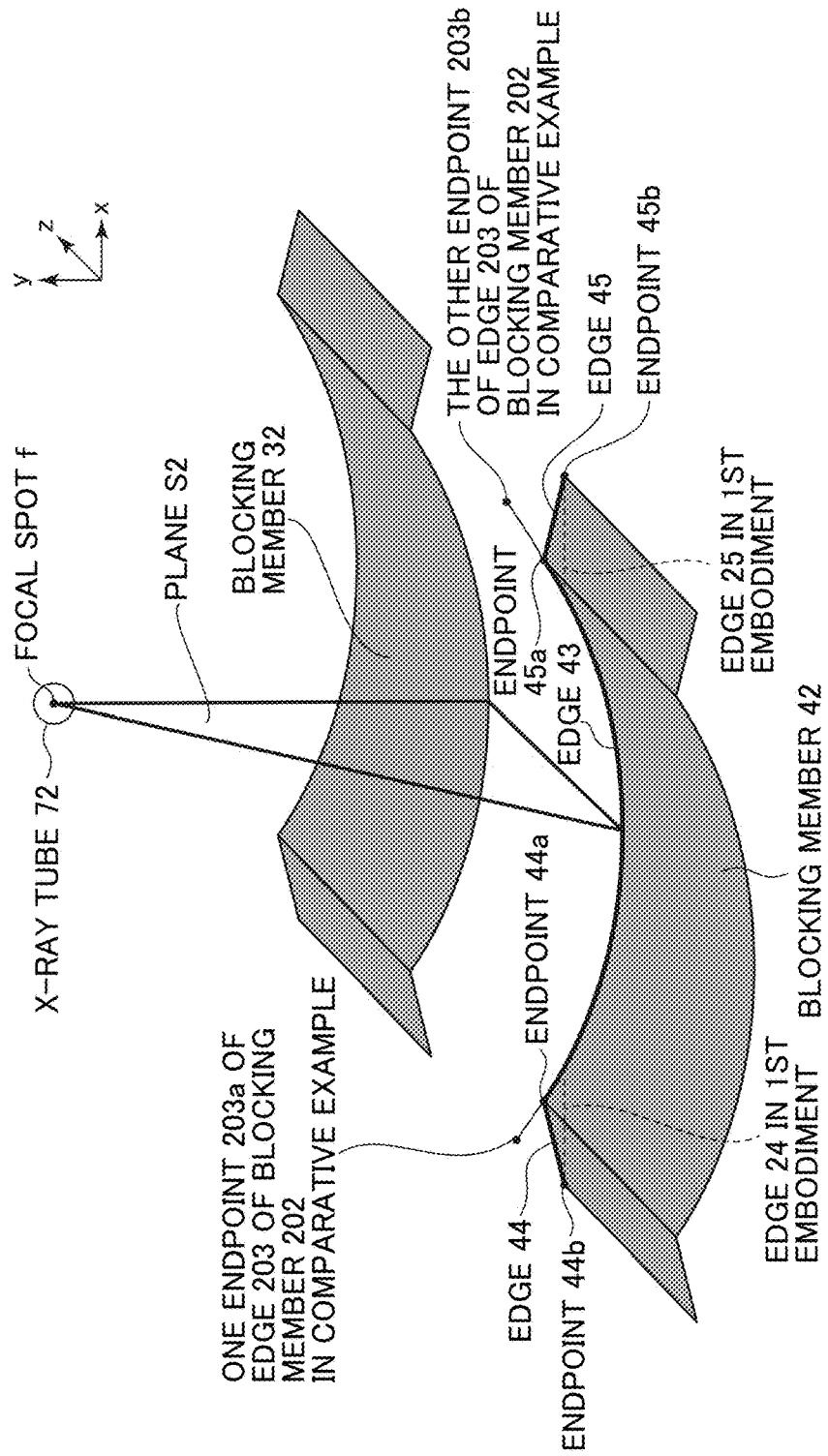
FIG. 33 is an enlarged perspective view of a blocking member 42 in FIG. 29.
Figure 34:
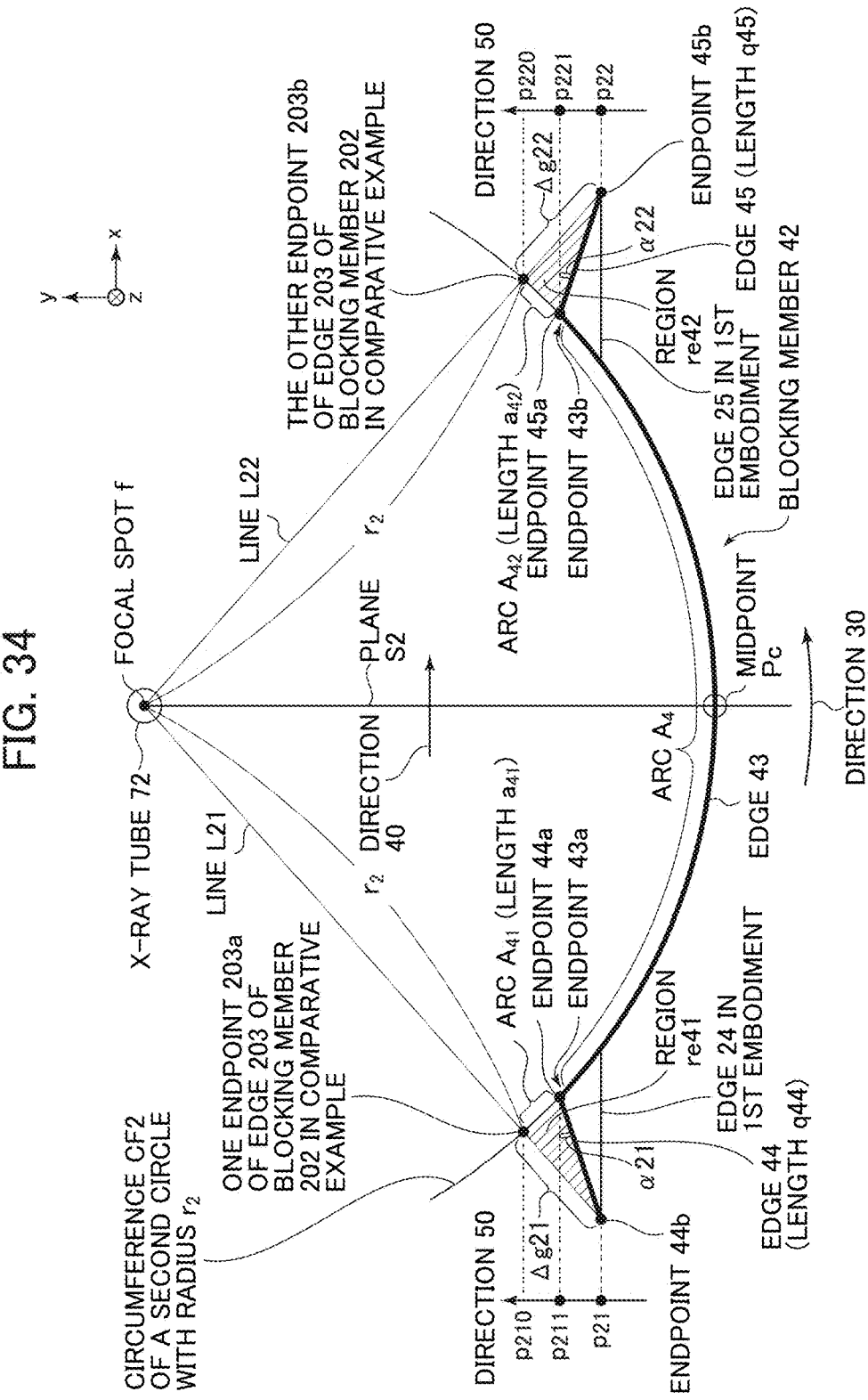
FIG. 34 is a diagram showing the shape of edges of the blocking member 42 in the XY-plane.

FIGS. 33 and 34 are explanatory diagrams for edges of the blocking member 42.

FIG. 33 is an enlarged perspective view of the blocking member 42, and FIG. 34 is a diagram showing the shape of the edges of the blocking member 42 in the XY-plane.

The blocking member 42 has an edge 43, an edge 44, and an edge 45.

As shown in FIG. 34, the edge 43 of the blocking member 42 is formed on an arc A4 lying on the circumference CF2 of the second circle with radius r2 around the focal spot f in the XY-plane. Therefore, the edge 43 of the blocking member 42 lies on the circumference CF2 of the second circle with radius r2, which is similar to the edge 203 of the blocking member 202 in the comparative example (see FIG. 15) in this regard. The edge 43 of the blocking member 42 in the second embodiment, however, is formed to be shorter than the edge 203 of the blocking member 202 in the comparative example. In FIGS. 33 and 34, the one endpoint 203a and the other endpoint 203b of the edge 203 of the blocking member 202 in the comparative example are shown to clarify the difference between the length of the edge 43 of the blocking member 42 in the second embodiment and that of the edge 203 of the blocking member 202 in the comparative example. The edge 43 of the blocking member 42 in the second embodiment is formed to be shorter than the edge 203 of the blocking member 202 in the comparative example by the total length (a41+a42) of a length a41 of an arc A41 and a length a42 of an arc A42, the arcs A41 and A42 lying on the circumference CF2 of the second circle with radius r2. While a41 and a42 are set so that a41=a42 in the second embodiment, it is possible to set them so that a41≠a42. Moreover, in the second embodiment, a31 and a32 (see FIG. 32) and a41 and a42 (see FIG. 34) are set to satisfy the equation below:

$$a31=a32=a41=a42 \quad (3)$$

However, it is possible to set at least one of the lengths a31, a32, a41, and a42 to be different from the remaining lengths.

Moreover, the blocking member 42 in the second embodiment is formed to have two straight edges 44 and 45, in addition to the arcuate edge 43.

In FIG. 34 is shown the plane S2. The plane S2 shown in FIG. 34 is identical to the plane S2 shown in FIG. 32, which contains a midpoint PC of the edge 43 in the direction 30 along the circumference CF2, and the focal spot f, and also is parallel to the body-axis direction (z-direction). The edges 44 and 45 lie opposite to each other with respect to the plane S2.

Now the edges 44 and 45 will be described one by one.

The edge 44 is a straight edge (with length q44) extending from one end point 43a of the arcuate edge 43 obliquely to the direction 40 perpendicular to the plane S2, and is oblique to the direction 40 by an angle α21. The edge 44 has one endpoint 44a connected to the endpoint 43a of the arcuate edge 43 and the other endpoint 44b lying opposite to the one point 44a. The edge 44 is formed to have a position p211 of the endpoint 44a in the direction 50 higher than the position p21 of the endpoint 44b in the direction 50.

In FIG. 34 is also shown the line L21 projected on the XY-plane. The line L21 overlies the focal spot f and the one endpoint 203a of the edge 203 of the blocking member 202 in the comparative example in the XY-plane. In the second embodiment, the endpoint 44b of the edge 44 lies at a position on the line L21 projected on the XY-plane, the position being away from the one endpoint 203a of the edge 203 of the blocking member 202 in the comparative example by Δg21 toward the X-ray detector 75. Therefore, the edge 44 is formed to lie on the side of the X-ray detector 75 relative to the arc A41 contiguous to the arc A4. In FIG. 34, a region re41 surrounded by the arc A41, line L21, and edge 44 is hatched. Since the edge 203 of the blocking member 202 in the comparative example extends on the arc A41, when the blocking member 202 in the comparative example is used, an X-ray beam traveling toward the region re41 reaches the X-ray detector 75 without being blocked by the blocking member 202 in the comparative example. However, since in the blocking member 42 in the second embodiment, the edge 44 is formed on the side of the X-ray detector 75 relative to the arc A41, when the blocking member 42 in the second embodiment is used, the X-ray beam traveling toward the region re41 may be blocked by the portion of the edge 44 of the blocking member 42. Therefore, a penumbra region PR41 may be formed in the corner 753 of the detector 75 (see FIGS. 29 and 30). The endpoint 44a of the edge 44 corresponds to a vertex v41 of the penumbra region PR41. Therefore, a side S41 of the penumbra region PR41 in the direction 40 (x direction) may be adjusted to a desired length by adjusting the position p211 of the endpoint 44a of the edge 44 in the direction 50 (see FIG. 34). For example, as the position p211 of the endpoint 44a of the edge 44 in the direction 50 is heightened, the endpoint 44a of the edge 44 comes closer to the endpoint 203a of the edge 203 of the blocking member 202 in the comparative example, causing the vertex v41 of the penumbra region PR41 to come closer to a vertex v410. Thus, by heightening the position p211 of the endpoint 44a of the edge 44 in the direction 50, the side S41 of the penumbra region PR41 may be shortened. On the other hand, as the position p211 of the endpoint 44a of the edge 44 in the direction 50 is lowered, the endpoint 44a of the edge 44 goes farther away from the endpoint 203a of the edge 203 of the blocking member 202 in the comparative example, causing the vertex v41 of the penumbra region PR41 to go farther away from the vertex v410. Thus, by lowering the position p211 of the endpoint 44a of the edge 44 in the direction 50, the side S41 of the penumbra region PR41 may be lengthened.

Moreover, a side S411 of the penumbra region PR41 in the direction 20 (z direction) may be shortened by narrowing the angle α21 while fixing the position of the endpoint 44a of the edge 44; on the other hand, the side S411 of the penumbra region PR41 may be lengthened by widening the angle α21 while fixing the position of the endpoint 44a of the edge 44.

In FIGS. 33 and 34, the edge 24 in the first embodiment is also shown as a reference to clarify the difference between the edge 44 in the second embodiment and the edge 24 in the first embodiment. The edge 44 in the second embodiment is formed to be oblique as compared with the edge 24 in the first embodiment by the angle α=α21.

Next, the edge 45 of the blocking member 42 will be described.

The edge 45 is a straight edge (with length q45) extending from the other endpoint 43b of the arcuate edge 43 obliquely to the direction 40 perpendicular to the plane S2, and is oblique to the direction 40 by an angle α22. The edge 45 has one endpoint 45a connected to the endpoint 43b of the arcuate edge 43 and the other endpoint 45b lying opposite to the one point 45a. The edge 45 is formed to have a position p221 of the endpoint 45a in the direction 50 higher than the position p22 of the endpoint 45b in the direction 50. While the length q45 of the edge 45 is equal to the length q44 of the edge 44 (q44=q45) in the second embodiment, it is possible to set so that q44≠q45. In the second embodiment, the lengths q34 and q35 of the edge 34 and edge 35 (see FIG. 32) and the lengths q44 and q45 of the edges 44 and 45 (see FIG. 34) are set to satisfy the equation below:

$$Q34=q35=q44=q45 \qquad (4)$$

However, it is possible to set at least one of the lengths q34, q35, q44, q45 to be different from the remaining lengths.

In FIG. 34 is also shown the line L22 projected on the XY-plane. The line L22 overlies the focal spot f and the other endpoint 203b of the edge 203 of the blocking member 202 in the comparative example in the XY-plane. In the second embodiment, the endpoint 45b of the edge 45 lies at a position on the line L22 projected on the XY-plane, the position being away from the other endpoint 203b of the edge 203 of the blocking member 202 in the comparative example by Δg22 toward the X-ray detector 75. Therefore, the edge 45 is formed to lie on the side of the X-ray detector 75 relative to the arc A42 contiguous to the arc A4. In FIG. 34, a region re42 surrounded by the arc A42, line L22, and edge 45 is hatched. Since the edge 203 of the blocking member 202 in the comparative example extends on the arc A42, when the blocking member 202 in the comparative example is used, an X-ray beam traveling toward the region re42 reaches the X-ray detector 75 without being blocked by the blocking member 202 in the comparative example. However, since in the blocking member 42 in the second embodiment, the edge 45 is formed on the side of the X-ray detector 75 relative to the arc A42, when the blocking member 42 in the second embodiment is used, the X-ray beam traveling toward the region re42 may be blocked by the portion of the edge 45 of the blocking member 42. Therefore, a penumbra region PR42 may be formed in the corner 754 of the detector 75 (see FIGS. 29 and 30). The endpoint 45a of the edge 45 corresponds to a vertex v42 of the penumbra region PR42. Therefore, a side S42 of the penumbra region PR42 in the direction 40 (x direction) may be adjusted to a desired length by adjusting the position p221 of the endpoint 45a of the edge 45 in the direction 50 (see FIG. 34). For example, as the position p221 of the endpoint 45a of the edge 45 in the direction 50 is heightened, the endpoint 45a of the edge 45 comes closer to the endpoint 203b of the edge 203 of the blocking member 202 in the comparative example, causing the vertex v42 of the penumbra region PR42 to come closer to a vertex v420. Thus, by heightening the position p221 of the endpoint 45a of the edge 45 in the direction 50, the side S42 of the penumbra region PR42 may be shortened. On the other hand, as the position p221 of the endpoint 45a of the edge 45 in the direction 50 is lowered, the endpoint 45a of the edge 45 goes farther away from the endpoint 203b of the edge 203 of the blocking member 202 in the comparative example, causing the vertex v42 of the penumbra region PR42 to go farther away from the vertex v420. Thus, by lowering the position p221 of the endpoint 45a of the edge 45 in the direction 50, the side S42 of the penumbra region PR42 may be lengthened.

Moreover, a side S421 of the penumbra region PR42 in the direction 20 (z direction) may be shortened by narrowing the angle α22 while fixing the position of the endpoint 45a of the edge 45; on the other hand, the side S421 of the penumbra region PR42 may be lengthened by widening the angle α22 while fixing the position of the endpoint 45a of the edge 45.

In FIGS. 33 and 34, the edge 25 in the first embodiment is also shown as a reference to clarify the difference between the edge 45 in the second embodiment and the edge 25 in the first embodiment. The edge 45 in the second embodiment is formed to be oblique as compared with the edge 25 in the first embodiment by the angle α=α22. While the angle α21 of the edge 44 and the angle α22 of the edge 45 are set so that $α_{21}=α_{22}$ in the second embodiment, it is possible to set them so that $α_{21} \neq α_{22}$.

As described above referring to FIGS. 29 to 34, the blocking members 32 and 42 in the second embodiment have the edges 34, 35, 44, and 45 on the side of the X-ray detector 75 relative to the arcs A31, A32, A41, and A42, and thus, X-ray beams traveling toward the regions re31, re32, re41, and re42 may be blocked. Therefore, as shown in FIGS. 29 and 30, the X-ray detector 75 may be provided in its four corners with the penumbra regions PR31, PR32, PR41, and PR42 corresponding to the regions re31, re32, re41, and re42. Thus, beam tracking may be still applied when the aperture width W is set to W=Wm (see FIG. 16).

As shown in FIG. 30, the edges 33, 34, and 35 of the blocking member 32 collinearly extend in the direction 40 in a plane (corresponding to ZX-plane in FIG. 30) perpendicular to the XY-plane and the plane S2, and the edges 43, 44, and 45 of the blocking member 42 likewise collinearly extend in the direction 40 in the plane (corresponding to ZX-plane in FIG. 30) perpendicular to the XY-plane and the plane S2. Thus, it is unnecessary to provide the blocking members 32 and 42 with the protrusions e1 to e4 (see FIG. 18) for forming penumbra regions, and therefore, the penumbra regions may be created without a limitation on the aperture width W1 (see FIG. 18) otherwise imposed when the protrusions e1 to e4 are provided.

In the second embodiment, the side S311 of the penumbra region PR31 and the side S321 of the penumbra region PR32 may be adjusted to desired lengths based on values of the angles α=α11 and α=α12 of the edges 34 and 35 of the blocking member 32 (see FIG. 32). Likewise, the side 5411 of the penumbra region PR41 and the side S421 of the penumbra region PR42 may be adjusted to desired lengths based on values of the angles α=α21 and α=α22 of the edges 44 and 45 of the blocking member 42 (see FIG. 34).

(3) Third Embodiment

As compared with the blocking members in the first embodiment, blocking members in a third embodiment are similar in shape of edges in the XY-plane but different in shape thereof in the ZX-plane. Therefore, in describing the third embodiment, description of the shape of the edges in the XY-plane will be omitted and the shape of the edges in the ZX-plane will be mainly described.

Figure 35:
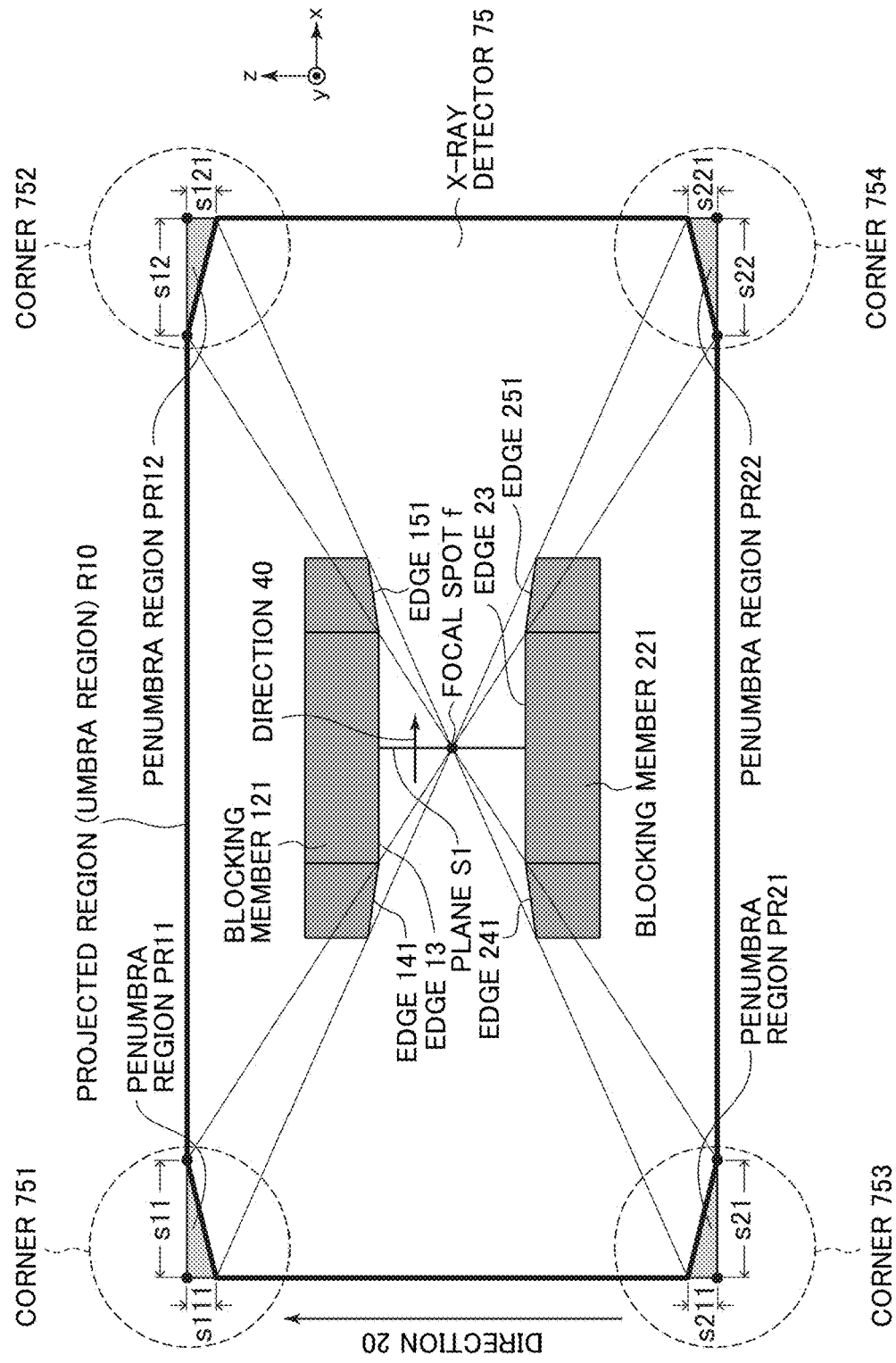
FIG. 35 is a plan view of the X-ray detector 75 and blocking members 121 and 221 in a ZX-plane.
Figure 36:
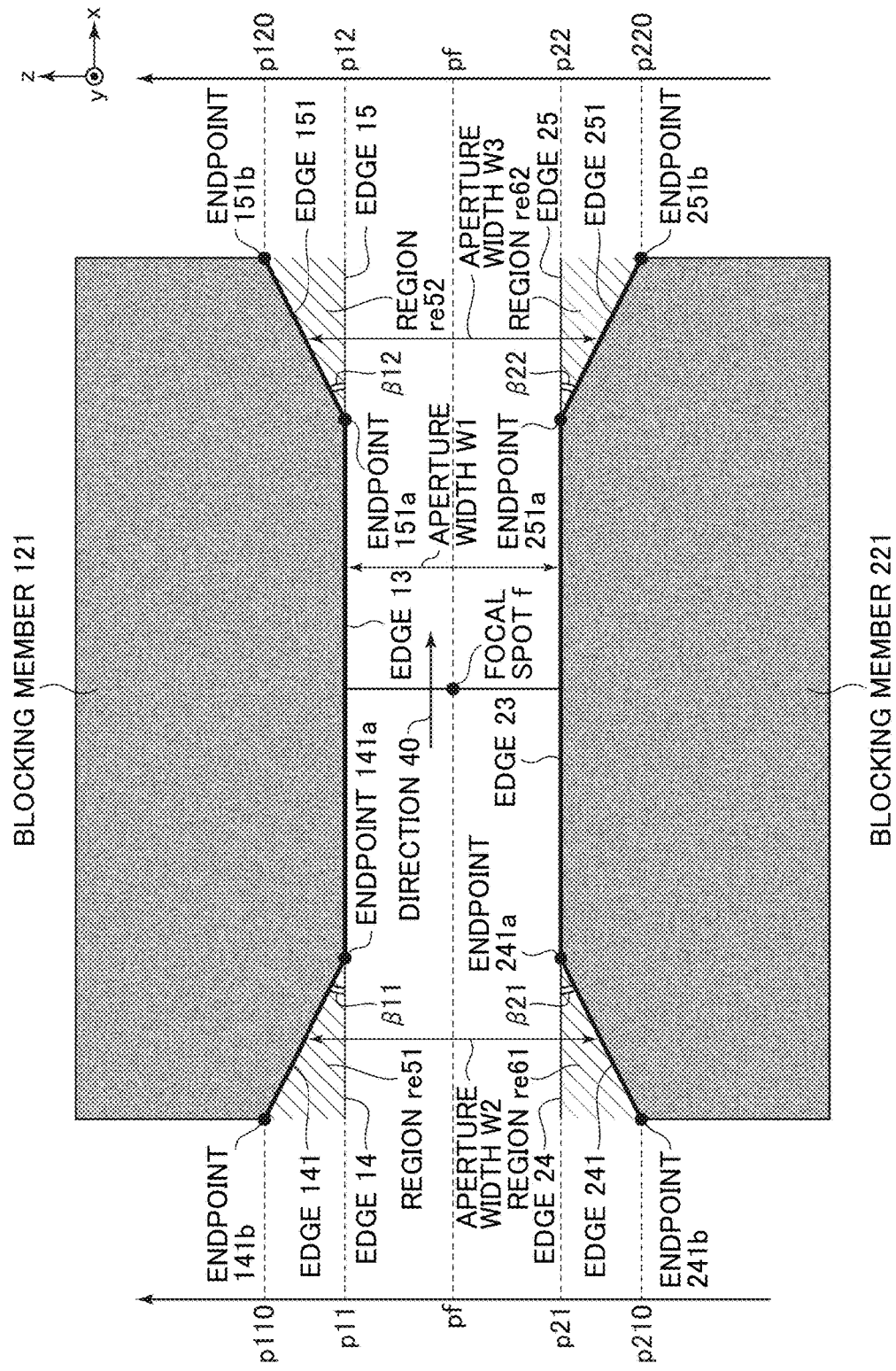
FIG. 36 is an enlarged view of the blocking members 121 and 221 in the ZX-plane.

FIGS. 35 and 36 are explanatory diagrams for edges of blocking members 52 and 62 in the third embodiment. Now the drawings will be described.

FIG. 35 is a plan view of the X-ray detector 75 and blocking members 121 and 221 in the ZX-plane, and FIG. 36 is an enlarged view of the blocking members 121 and 221 in the ZX-plane.

Of the edges that the blocking member 121 in the third embodiment has, edges similar to those of the blocking member 12 in the first embodiment are designated by similar symbols in FIGS. 35 and 36 for convenience of explanation. Likewise, of the edges that the blocking member 221 in the third embodiment has, edges similar to those of the blocking member 22 in the first embodiment are designated by similar symbols.

The blocking member 121 will be described first.

The blocking member 121 has an edge 13, an edge 141, and an edge 151.

The edge 13 of the blocking member 121 is similar to the edge 13 of the blocking member 12 in the first embodiment. However, the edges 141 and 151 of the blocking member 121 are different from the edges 14 and 15 of the blocking member 12 in the first embodiment. Accordingly, description of the edge 13 of the blocking member 121 will be omitted and the edges 141 and 151 will be particularly described below.

The edge 141 has one endpoint 141a connected to one endpoint of the edge 13 and the other endpoint 141b lying opposite to the one endpoint 141a. In FIG. 36, the z-positions of the endpoints 141a and 141b of the edge 141 are designated by symbols "p11" and "p110," respectively. Representing the z-position of the focal spot f as "pf," the z-position p110 of the endpoint 141b of the edge 141 is farther away from the z-position pf of the focal spot f than the z-position p11 of the endpoint 141a of the edge 141 is. In FIG. 36, the edge 14 in the first embodiment is also shown as a reference to clarify the difference between the edge 141 in the third embodiment and the edge 14 in the first embodiment. While the edge 14 in the first embodiment is formed to be collinear with the edge 13 in a plane (corresponding to ZX-plane in FIG. 36) perpendicular to the XY-plane and the plane S1, the edge 141 in the third embodiment is formed to be oblique to the edge 13 by an angle β11. Therefore, when the blocking member 12 in the first embodiment is used, an X-ray beam traveling toward a region re51 is blocked, whereas when the blocking member 121 in the third embodiment is used, the X-ray beam traveling toward the region re51 may reach the X-ray detector 75 without being blocked. Thus, when the blocking member 121 in the third embodiment is used, a side S111 of the penumbra region PR11 in the direction 20 (z direction) (see FIG. 35) may be lengthened by narrowing the angle β11 of the edge 141 while fixing the position of the endpoint 141a of the edge 141; on the other hand, the side S111 of the penumbra region PR11 may be shortened by widening the angle 1311 while fixing the position of the endpoint 141a of the edge 141.

Next, the edge 151 will be described.

The edge 151 has one endpoint 151a connected to the other endpoint of the edge 13 and the other endpoint 151b lying opposite to the one endpoint 151a. In FIG. 36, the z-positions of the endpoints 151a and 151b of the edge 151 are designated by symbols "p12" and "p120," respectively. The z-position p120 of the endpoint 151b of the edge 151 is farther away from the z-position pf of the focal spot f than the z-position p12 of the endpoint 151a of the edge 151 is. In FIG. 36, the edge 15 in the first embodiment is also shown as a reference to clarify the difference between the edge 151 in the third embodiment and the edge 15 in the first embodiment. While the edge 15 in the first embodiment is formed to be collinear with the edge 13 in the plane (corresponding to ZX-plane in FIG. 36) perpendicular to the XY-plane and the plane S1, the edge 151 in the third embodiment is formed to be oblique to the edge 13 by an angle β12. Therefore, when the blocking member 12 in the first embodiment is used, an X-ray beam traveling toward a region re52 is blocked, whereas when the blocking member 121 in the third embodiment is used, the X-ray beam traveling toward the region re52 may reach the X-ray detector 75 without being blocked. Thus, when the blocking member 121 in the third embodiment is used, a side S121 of the penumbra region PR12 in the direction 20 (z direction) (see FIG. 35) may be lengthened by narrowing the angle β12 of the edge 151 while fixing the position of the endpoint 151a of the edge 151; on the other hand, the side S121 of the penumbra region PR12 may be shortened by widening the angle β12 while fixing the position of the endpoint 151a of the edge 151.

Next, the blocking member 221 will be described.

The blocking member 221 has an edge 23, an edge 241, and an edge 251.

The edge 23 of the blocking member 221 is similar to the edge 23 of the blocking member 22 in the first embodiment. However, the edges 241 and 251 of the blocking member 221 are different from the edges 24 and 25 of the blocking member 22 in the first embodiment. Accordingly, description of the edge 23 of the blocking member 221 will be omitted, and the edges 241 and 251 will be particularly described below.

The edge 241 has one endpoint 241a connected to one endpoint of the edge 23 and the other endpoint 241b lying opposite to the one endpoint 241a. In FIG. 36, the z-positions of the endpoints 241a and 241b of the edge 241 are designated by symbols "p21" and "p210," respectively. The z-position p210 of the endpoint 241b of the edge 241 is farther away from the z-position pf of the focal spot f than the z-position p21 of the endpoint 241a of the edge 241 is. In FIG. 36, the edge 24 in the first embodiment is also shown as a reference to clarify the difference between the edge 241 in the third embodiment and the edge 24 in the first embodiment. While the edge 24 in the first embodiment is formed to be collinear with the edge 23 in the plane (corresponding to ZX-plane in FIG. 36) perpendicular to the XY-plane and the plane S1, the edge 241 in the third embodiment is formed to be oblique to the edge 23 by an angle β21. Therefore, when the blocking member 22 in the first embodiment is used, an X-ray beam traveling toward a region re61 is blocked, whereas when the blocking member 221 in the third embodiment is used, the X-ray beam traveling toward the region re61 may reach the X-ray detector 75 without being blocked. Thus, when the blocking member 221 in the third embodiment is used, a side S211 of the penumbra region PR21 in the direction 20 (z direction) (see FIG. 35) may be lengthened by narrowing the angle β21 of the edge 241 while fixing the position of the endpoint 241a of the edge 241; on the other hand, the side S211 of the penumbra region PR21 may be shortened by widening the angle β21 of the edge 241 while fixing the endpoint 241a of the edge 241.

Next, the edge 251 will be described.

The edge 251 has one endpoint 251a connected to the other endpoint of the edge 23 and the other endpoint 251b lying opposite to the one endpoint 251a. In FIG. 36, the z-positions of the endpoints 251a and 251b of the edge 251 are designated by symbols "p22" and "p220," respectively. The z-position p220 of the endpoint 251b of the edge 251 is farther away from the z-position pf of the focal spot f than the z-position p22 of the endpoint 251a of the edge 251 is. In FIG. 36, the edge 25 in the first embodiment is also shown as a reference to clarify the difference between the edge 251 in the third embodiment and the edge 25 in the first embodiment. While the edge 25 in the first embodiment is formed to be collinear with the edge 23 in the plane (corresponding to ZX-plane in FIG. 36) perpendicular to the XY-plane and the plane S1, the edge 251 in the third embodiment is formed to be oblique to the edge 23 by an angle β22. Therefore, when the blocking member 22 in the first embodiment is used, an X-ray beam traveling toward a region re62 is blocked, whereas when the blocking member 221 in the third embodiment is used, the X-ray beam traveling toward the region re62 may reach the X-ray detector 75 without being blocked. Thus, when the blocking member 221 in the third embodiment is used, a side S221 of the penumbra region PR22 in the direction 20 (z direction) (see FIG. 35) may be lengthened by narrowing the angle β22 of the edge 251 while fixing the position of the endpoint 251a of the edge 251; on the other hand, the side S221 of the penumbra region PR22 may be shortened by widening the angle β22 of the edge 251 while fixing the position of the endpoint 251a of the edge 251.

In the third embodiment, the angles β11, β12, β21, and β22 satisfy a relationship β11=β12=β21=β22. However, it is possible that at least one of the angles β11, β12, β21, and β22 has a different value from the other angles.

Moreover, the edges 13 and 23 are parallel with the direction 40. Therefore, the aperture width W1 between the edges 13 and 23 has the same value over the lengths of the edges 13 and 23. However, an aperture width W2 between the edges 141 and 241 has a greater value as it goes farther away from the focal spot f. Likewise, an aperture width W3 between the edges 151 and 251 has a greater value as it goes farther away from the focal spot f.

In the third embodiment, the side S111 of the penumbra region PR11 and side S121 of the penumbra region PR12 may be set to desired lengths based on valued of the angles β=β11 and β=β12 of the edges 141 and 151 of the blocking member 121 (see FIG. 36). Likewise, the side S211 of the penumbra region PR21 and side S221 of the penumbra region PR22 may be set to desired lengths based on valued of the angles β=β21 and β=β22 of the edges 241 and 251 of the blocking member 221 (see FIG. 36).

We claim:

1. An aperture used in an X-ray togomoraphic imaging apparatus, for defining an extent of X-rays in a body-axis direction, said X-ray togomoraphic imaging apparatus comprising:
    an X-ray tube; and
    an X-ray detector having a plurality of detector elements arranged in first and second directions, said first direction (10) being along a circumference of a first circle with radius r1 around a focal spot of said X-ray tube in a first plane (XY-plane) perpendicular to said body-axis direction, and said second direction (20) being parallel to said body-axis direction, said aperture comprising:
    a first blocking member for blocking X-rays;
    a second blocking member disposed in said second direction (20) with respect to said first member, for blocking X-rays, wherein each of said first and second blocking members has:
    a first edge formed on a first arc lying on a circumference of a second circle with radius r2 (<r1) around the focal spot of said X-ray tube in said first plane (XY-plane);
    a second edge connected to one endpoint of said first edge, said second edge being formed to lie on a side of said X-ray detector with respect to a second arc lying on the circumference of said second circle and contiguous with said first arc; and
    a third edge connected to another endpoint of said first edge, said third edge being formed to lie on the side of said X-ray detector with respect to a third arc lying on the circumference of said second circle and contiguous with said first circle on a side opposite to said second arc.

2. The aperture as recited in claim 1, wherein:
said second edge has a first endpoint connected to the one endpoint of said first edge and a second endpoint lying opposite to said first endpoint, and
said third edge has a third endpoint connected to the other endpoint of said first edge and a fourth endpoint lying opposite to said third endpoint.

3. The aperture as recited in claim 2, wherein: said second and third edges lie opposite to each other with respect to a second plane (S1, S2), said second plane containing a midpoint of said first edge in a direction (30) along the circumference of said second circle, and said focal spot, and being parallel to said body-axis direction.

4. The aperture as recited in claim 3, wherein: said first, second, and third edges are formed to collinearly extend in a third plane (ZX-plane) perpendicular to said first and second planes.

5. The aperture as recited in claim 3, wherein:
said second and third edges lie in parallel with a third direction (40) perpendicular to said second plane in said first plane (XY-plane).

6. The aperture as recited in claim 5, wherein:
a first aperture width is provided between the first edge of said first blocking member and the first edge of said second blocking member,
a second aperture width is provided between the second edge of said first blocking member and the second edge of said second blocking member, and
a third aperture width is provided between the third edge of said first blocking member and the third edge of said second blocking member.

7. The aperture as recited in claim 6, wherein:
said second aperture width and said third aperture width each have a greater value as it goes farther away from said focal spot in a third plane (ZX-plane) perpendicular to said first and second planes.

8. The aperture as recited in claim 3, wherein:
said second and third edges extend obliquely to a third direction (40) perpendicular to said second plane in said first plane (XY-plane).

9. The aperture as recited in claim 8, wherein:
said first and second endpoints of said second edge are different in position in a fourth direction (50) perpendicular to said body-axis direction and to said third direction, and
said third and fourth endpoints of said third edge are different in position in said fourth direction (50).

10. The aperture as recited in claim 9, wherein:
said second edge is formed to have a position of said first endpoint in said fourth direction (50) higher than that of said second endpoint in said fourth direction (50), and
said third edge is formed to have a position of said third endpoint in said fourth direction (50) higher than that of said fourth endpoint in said fourth direction (50).

11. A collimator having an aperture for defining an extent of X-rays in a body-axis direction and used in an X-ray togomoraphic imaging apparatus, said X-ray togomoraphic imaging apparatus comprising:

an X-ray tube; and
an X-ray detector having a plurality of detector elements arranged in first and second directions, said first direction (10) being along a circumference of a first circle with radius r1 around a focal spot of said X-ray tube in a first plane (XY-plane) perpendicular to said body-axis direction, and said second direction (20) being parallel to said body-axis direction, said aperture comprising:
a first blocking member for blocking X-rays;
a second blocking member disposed in said second direction with respect to said first member, for blocking X-rays, wherein each of said first and second blocking members has:
a first edge formed on a first arc lying on a circumference of a second circle with radius r2 (<r1) around the focal spot of said X-ray tube in said first plane (XY-plane);
a second edge connected to one endpoint of said first edge, said second edge being formed to lie on a side of said X-ray detector with respect to a second arc lying on the circumference of said second circle and contiguous with said first arc; and
a third edge connected to another endpoint of said first edge, said third edge being formed to lie on the side of said X-ray detector with respect to a third arc lying on the circumference of said second circle and contiguous with said first circle on a side opposite to said second arc.

12. An X-ray togomoraphic imaging apparatus comprising:
an X-ray tube;
an X-ray detector having a plurality of detector elements arranged in first and second directions, said first direction (10) being along a circumference of a first circle with radius r1 around a focal spot of said X-ray tube in a first plane (XY-plane) perpendicular to a body-axis direction, and said second direction (20) being parallel to said body-axis direction; and
an aperture defining an extent of X-rays in the body-axis direction, said aperture comprising:
a first blocking member for blocking X-rays;
a second blocking member disposed in said second direction with respect to said first member, for blocking X-rays, wherein each of said first and second blocking members has:
a first edge formed on a first arc lying on a circumference of a second circle with radius r2 (<r1) around the focal spot of said X-ray tube in said first plane (XY-plane);
a second edge connected to one endpoint of said first edge, said second edge being formed to lie on a side of said X-ray detector with respect to a second arc lying on the circumference of said second circle and contiguous with said first arc; and
a third edge connected to another endpoint of said first edge, said third edge being formed to lie on the side of said X-ray detector with respect to a third arc lying on the circumference of said second circle and contiguous with said first circle on a side opposite to said second arc.

* * * * *